United States Patent [19]
Leskovar

[11] Patent Number: 6,156,312
[45] Date of Patent: Dec. 5, 2000

[54] AGENTS, AFFECTING THE HYPERACTIVATED IMMUNOLOGICAL EFFECTOR CELLS

[76] Inventor: Peter Leskovar, Tizianstrasse 3c, 83026 Rosenheim, Germany

[21] Appl. No.: 08/564,370
[22] PCT Filed: Jun. 19, 1994
[86] PCT No.: PCT/EP94/01992
  § 371 Date: Jan. 18, 1996
  § 102(e) Date: Jan. 18, 1996
[87] PCT Pub. No.: WO95/00175
  PCT Pub. Date: Jan. 5, 1995

[30] Foreign Application Priority Data

Jun. 23, 1993 [DE] Germany ............................... 43 20 878
Jul. 25, 1993 [DE] Germany ............................... 43 24 877
Apr. 7, 1994 [DE] Germany ............................... 44 11 956

[51] Int. Cl.[7] .................................................. A61K 39/395
[52] U.S. Cl. ........................................................ 424/144.1
[58] Field of Search ...................... 424/144.1; 530/389.1, 530/389.7

[56] References Cited

PUBLICATIONS

Viswanathan, K.N., et al. 1991. Cephalalgia, vol. 11 Supplement 11, pp. 166–167. "Cinnarizine–propanalol In Migraine Prophylaxis . . .".

Mayumi, H., Good, R.A. 1989. J. Experimental Medicine. vol. 169 pp. 213–238. "Long–Lasting Skin Allograft Tolerance in Adult . . . ".

Thomas, E.D., et al. 1975. New England Journal of Medicine. vol. 292, No. 16, pp. 832–843. "Bone Merrow Transplantation (First of two parts)".

*Primary Examiner*—Remy Yucel
*Attorney, Agent, or Firm*—Needle & Rosenberg, P.C.

[57] ABSTRACT

A method to reduce hyperactivated immunologic effector cells involves the administration (I) a Ca-antagonist and (II) an agent, to reduce the intracellular cAMP/cGMP-ratio. A treatment for eliminating the hyperactivated effector cells utilizes a combination of an agent to eliminate the hyperactivated effector cells and alloreactive cells with predetermined cell death.

13 Claims, No Drawings

AGENTS, AFFECTING THE HYPERACTIVATED IMMUNOLOGICAL EFFECTOR CELLS

BACKGROUND OF THE INVENTION

The invention deals with an agent, able to affect the hyperactivated immununological effector cells and with its use.

Different situations and disorders of humans are associated with a hyperactivated state of the immunological effector cells, caused e.g. by cytokines; such effector cells lose their ability to respond to new specific signals. The immune system is impaired or even switched off in such situations. This occurs e.g. following a persistent stimulation during a prolonged infection or in situations of cell hyperactivation due to an excessive release of endogenous cytokines. The term "immunological effector cells" comprises e.g. T cells, macrophages/monocytes, NK cells and other immunological cells.

A variety of immunological processes include on the cellular level the cyclic adenosine phosphate (cAMP) which is produced by the enzyme adenylate cyclase (AC) from adenosine triphosphate (ATP). The cAMP plays as "second messenger" a central role in the hormonal regulation as well as in the metabolism (through activation of protein kineses, e.g. protein kinase A (PKA). The PKA phosphorylates proteins which in turn depress the immune response. In this way, the hyperactivation of effector cells results in the down regulation of the immune function.

This reaction cascade is regulated by the production of cyclic guanosine monophosphate (cGMP) which antagonizes the cAMP. This reaction cascade is also influenced by the group of G-protein coupled receptors, comprising receptors such as adrenergic, muscarinic, histamine, serotonin and adenosine receptors. The G-proteins (guanine nucleotide-binding proteins) are able to stimulate (Gs) or to inhibit (Gi) the production of second messengers. By affecting either the Gs- or the Gi-receptors, the stimulation of AC and herewith the cAMP-production can be regulated. Situations with a disturbed equilibrium are e.g. cancer, viral diseases and autoimmune disorders, as well as the inducing and disease-maintaining component of the atherosclerosis.

SUMMARY OF THE INVENTION

The objective of the invention was to provide an agent, able to fight with such disorders and to restore the susceptibility of the hyperactivation-depressed immune system for signals and a normal immune response. This objective can be achieved by an agent, capable to affect the hyperactivated immunological effector cells which comprises (I) a Ca-antagonist, and (II) an agent, able to decrease the intracellular cAMP/cGMP-ratio. Surprisingly, it could be found out that such a combination reduced or prevented the hyperactivation of effector cells. In this way, these cells re-acquire their susceptibility for specific signals and show a normal immune reaction. It could be shown that hyperactivated cells contain an excess of calcium ions and are characterized by an increased cAMP/cGMP-ratio.

According to the invention, the principle of the agent is the prevention of $Ca^{2+}$-influx and reduction of cAMP/cGMP-ratio in immune effector cells. This can be achieved by the combination of component I and II. Surprisingly, in this way, diseases as different as cancer, autoimmune disorders, arteriosclerosis which seems to need an autoimmune promotor for its provocation, further bacterial, viral, including retro viral infections, as well as some "modern" diseases, based on immunological derailment or deviations, e.g. the CFS (chronic fatigue syndrome) can be treated. All these situations and disorders appear to contain—in the immunological sense—common disregulation elements. These common elements are e.g. a persistent or excessive activation of certain leukocyte-subpopulations, mostly macrophages and helper T cells, as well as suppressor cells. During a simultaneous hyperactivation of macrophages and helper T cells, as observed in HIV-patients, a mutual stimulation of both interdependent leukocyte-subpopulations can occur.

A further common element is the deblockade of blastogenically pretransformed T4 and plasma (B) cells as consequence of preceding, persistent latent or manifest immunosuppression; it is based on a "critical drop" of autoantigen or pathogen-specific surveyor cells or suppressor T cells. From the molecular-biologic point of view, the persistence of an increased intracellular $Ca_i^{2+}$-level, leading to an immunosuppressive counter regulation and to an impaired sensitivity to new antigenic signals, is a common element of a variety of disorders mentioned above. This results not only in the impairment of the existent set of immunocompetent cells but, in addition, in a disturbed recruitment of new, intact immunocytes.

The combination of components I and II, according to the invention, deblocks the misprogrammed immunocytes or effector cells, primarily those in the hyperactivated state, and has therefore impact on the "wound healing" or "tissue repair"-function of misprogrammed macrophages and cytokine-hyper secreting helper T cells. This hyperactivated or persistently activated state of effector cells can be prevented through component I by breaking the $Ca^{2+}$-rigidity, i.e. by breaking the $Ca_i^{2+}$-overload of effector cells; on the other hand, the $Ca_i^{2+}$-level is regulated by the intracellular pHi. An additional mechanism is the control of the electrolyte transport through the cell membrane, i.e. the regulation of the $Ca^{2+}$-, $Na^+$- and $K^+$-channels and of the $Na^+/K^+$-, $Na^+/H^+$-, $K^+/H^+$-, $HCO_3^-/Cl^-$ and $Ca^{2+}/Na^+$-antiport, symport and different ATPases, respectively. According to the invention, the combination was able to reduce the primary tumor and metastases in cancer patients by ⅓ to ⅔ within few weeks, without a simultaneous radio- or chemotherapy.

The CFS-patients also showed surprising therapeutic results. Here presented examples of component I and II can be combined as well. Their effect in patients with neoplastic and autoimmune diseases, atherosclerosis, amyloidosis, Alzheimer disease and CFS can further be potentiated by combining them with known immunostimulators and BRMs. In addition, these combinations can be used therapeutically in bacterial and viral infections. Herewith, the initial derailment, i.e. the hyperactivation of leukocyte-subpopulations can be reversed. The restoration of the original immune state then occurs spontaneously.

The therapeutic protocol can consist of 2 or 3 steps. So, in the first phase a deblockade of immunocompetent, misprogrammed effector cells, primarily macrophages and T cells, can occur, and in the second phase, a controlled stimulation of immunocytes can follow.

In a further modification, a "freezing-up" of the controlled stimulated cell state, i.e. a prolongation of the second phase (phase 3) is foreseen. In the first phase, the drug combination, according to the invention, is used. In the second phase, well known immunostimulators and in the third phase, the same combination as in the first phase, but at reduced concentration, e.g. 20 to 50% of the concentration, used in the first phase, are foreseen.

DETAILED DESCRIPTION OF THE SEVERAL EMBODIMENTS

Details about the deblocking of immunocompetent cells in hypoxia and/or acidified milieu of chronically inflammated tissues, including necrotic tumor tissue are described.

Hyper- or persistently activated macrophages consume up to 10–20 times more oxygen than resting macrophages; in the presence of gamma-interferon, this $O_2$-consumption increases additionally.

The phagocytosis of opsonized particles (bacteria, latex etc.) as well as of immune complexes via the Fc-gamma-receptor switches on the Embden-Mayerhof-glycolysis pathway. Herewith, the generation of the microbicidal oxygen radicals (ROI) from molecular oxygen is stimulated. In addition, the synthesis of leukotriens C, D and E (via reduced glutathione) is impaired due to a direct electron and proton transfer on $O_2$-radicals (mediated by cytochrome P450). Leukotrien B which is synthesized instead of the leukotriens C, D and E stimulates directly the cytochrome P450-mediated ROI-generation.

The glycolysis leads via the excessive production and secretion of lactic acid to a strong acidification of the macrophage micro milieu. The pH-drop results in the suppression of immunocyte function. The impaired synthesis of Leukotrien C, D and E, additionally affected by ROI, results in an inhibited glycosylation and secretion of cytokines and immunoglobulins.

The hypoxia inflammation tissue, e.g. necrotic tumor tissue, caused by the impaired angiogenesis and hyperactivated macrophages leads to pH-drop which results in cell depression (below pH 6,8) and cell death at a continued pH-drop.

Both, the apoptotic and the autolytic cell death appear to arise from the drop of intracellular pH which is associated with the activation of lysosomal enzymes. A defect in the $H^+$-pump which maintains a lysosomal pH of 4,5–5,0 precedes the cell death.

As known from the myocard cells, the cell death is accelerated in the presence of oxygen as terminal electron acceptor if the cell is activated and herewith the intracellular $Ca_i$-level is increased. Therefore, under hypoxic or ischemic conditions, the glucose catabolism via the TCC/citrate cycle should be inhibited by special drugs. Herewith, the overproduction of $NADH_2$ (and $NADPH_2$) which leads to an accelerated glycolytic lactate synthesis and to pH drop, can be prevented. For this reason, BRMs have to be combined with deblocking substances, or the deblocking of immunocompetent cells has to precede other (immuno)therapeutic steps. The component II comprises an agent which is able to affect the cAMP/cGMP-ratio. One variant proposes the increase of intracellular cGMP-level.

One of the main reasons for the blocked function of immunocompetent cells (mononuclear and polymorphonuclear phagocytes, NK cells, K cells, T cells) in situ/in vitro e.g. in tumor lesions or in chronic inflammation tissues is the low cGMP-level or the increased cAMP-level in the cytosol of immunocompetent cells.

The increased cAMP-level arises primarily from the activation of adenylate cyclase by hyperproduced prostaglandins (PGE2/E1); these prostaglandins are secreted by hyperactivated macrophages, fibroblasts and synovial cells. They activate, together with catecholarnines, the enzyme adenylate cyclase which results in cAMP-increase in cytosol.

The intracellular cAMP-rise inhibits different cell functions of various immunocyte subclasses. Therefore the induction of guanylate cyclase and herewith the cGMP-rise in immunocompetent cells is recommended according the invention. In this way, the blocked (preinactivated) effector cells switch their function from the suppressor to the effector.

According to the invention, the following agents can be used therapeutically (a) as single agents, or (b) combined with each other, or (c) combined as single agents or as mutual combinations (see (b)) with different BRMs:

(1) alkalizing substances, such as alkali-(bi)carbonate and alkali-salts of metabolizable organic acids (e.g. Nalactate, Na-gluconate, Na-, K-citrate).

(2) reversible competitive inhibitors of citrate oxidation in Krebs/citrate cycle, i.e. inhibitors of tricarboxylic acids in citrate cyclus (e.g. tricarballylate, methyl/ethyl-succinate, malonate etc.). The working mechanism is the prevention of cell (e.g. macrophage) hyperactivation in situations, associated with $O_2$-deficit.

(3) β-blockers in general. The working mechanism is the inhibition of intracellular cAMP-rise and of A-kinase (PKA) -activity.

(4) Ca-antagonists in general. The working mechanism is the inhibition of $Ca^{2+}$-influx into the hyperactivated (hypoxic) cell which prevents the $Ca_i$-stimulated oxidation in Krebs cycle during $O_2$-deficit and herewith the cell death. In the case of hyperactivated macrophages, the ROI generation can be inhibited in this way. These ROIs block in turn the glycosylation and secretion of cytokines.

(5) Ca-agonists in general. The working mechanism is like in the case of β-blocker (point (3)), the $Ca_i$-increase. The following 2-step-protocol is recommended: first, the activity of the "misprogrammed", i.e. hyperactivated macrophages has to be blocked by Ca-antagonists (point (4)); the $2^{nd}$ step is the activation of immunocompetent cells by Ca-agonists and/or β-blockers.

(6) Substances, preventing pHi-drop by penetrating into the cell and binding the excessive $H^+$-ions. This class of substances comprises all representatives of alkaline compounds, e.g. derivatives of TRIZMA, HEPES, mono-, di- and triethanolamines, as well as chloroquine and other antimalaria drugs, further monensin and compounds which are able to release $NH_3$ intracellularly, such as glutamine and asparagine. Further $pH_i$-increasing substances are LI-, Cs- and Rb-salts of carbonic acid and organic acids. The weak bases have to be used as free bases, as (bi)carbonate or as salts of metabolizable organic acids, but not as chloride, sulfate, nitrate etc. These substances can be combined with alkali-salts of metabolizable organic,acids (see point (1)) and/or with inhibitors of TCC/citrate cycle.

(7) Inhibitors of LDH (lactate dehydrogenase) and XOD (xanthin oxydase). The working mechanism is the inhibition of lactate production which prevents the excessive acidification of cytosol and extracellular milieu. These LDH- and XOD-inhibitors can be combined with inhibitors of TCC/Krebs-cycle.

(8) Substances, able to correct the intracellular redox-potential, e.g. fumarate/maleinate, vitamin C, vitamin A, vitamin E, alkali (K)-ferrocyanide, Se-compounds (e.g. Na-selenite), Na-/K-thiosulfate, alkali-sulfate and compounds carrying reduced forms of mercaptylt/thionyl (—SH)-groups, e.g. glutathione, penicillamine, thiola (thiopronine), cysteine, methionine etc.

(9) Substances, correcting the intracellular $NAD(P)^+/NAD(P)H_2$- or the $GSSG/2GSH$-ratio, e.g. N-acetyl cysteine.

(10) Substances, replacing the terminal electron-acceptor (molecular $O_2$) of the oxidative phosphorylation, e.g. ascorbate, dehydroascorbate, insaturated fatty acids.

(11) ROI-scavengers and/or antioxidants, e.g. (a) phenols such as tocopherols, flavonoids, phenolic acid plus esters, benzodioxols, lignanes (NDGA), BHT, BRA, THBP (b) amines such as tetramethyl-p-phenylenediamine (c) heterocyclic compounds such as ethoxyquinine, barbiturates, carbazols, phenothiazines, levamisole, nafazatron, naloxone and tinoridine (d) different compounds such as vitamin C, glutathione (GSH), β-carotine and vitamine A-derivatives.
(12) Cl$^-$-channel blockers.
(13) Cyclooxygenase inhibitors/NSAIDs.
(14) H$_2$-specific antihistaminics (antagonists of the H$_2$-histamine receptor), e.g. cimetidine.
(15) inhibitors of the cAMP- and cGMP-phosphodiesterase (methylxanthines; e.g. theophylline or theobromine.
(16) Since the immune complexes (IC) suppress—via special receptors, such as the Fc(gamma)-R and/or CR1, CR3, CRq and other receptors—both the macrophages/monocytes and NK cells and stimulate suppressor T cells (T$_G$/Ts), the IC interaction with immunocyte receptors has to be blocked, according to the invention, (a) by the Fc(gamma)-subunit of Ig (IgG), (b) by the biotechnologically modified complement subunits (replacement of key amino acids), e.g. c3b, c3bi or clq and/or (c) by an IgG-excess.
(17) Substances, acting anti-denaturing and partially re-naturing on biorelevant proteins, e.g. formamide, acetamide, anilide (fomlanilide, acetanilide), and their alkyl- and dialkyl derivatives, especially the non-toxic mono methyl-derivatives and other water-miscible compounds. They act by weakening the hydration and the dielectric constant (DK) of the medium. These substances can be combined with PEG, PVP and/or DMSO. The same substances and their combinations with PEG, PVP, glycerol and/or DMSO are at the same time, according to the invention, highly efficient cryoprotectants for cells and proteins. The PVP seems to be non-toxic, as it has been clinically used for years as plasma expander. Each class of the above described deblocking substances can also be used as additive to conventional vaccines.
(18) Anti-gamma-interferon, anti-M-CSF, anti-GM-CSF and anti-TNFalpha.
(19) Liposomes, containing (a) cytotoxic agents (b) other cytotoxins, e.g. ricin, abrin.
(20) Substances, preventing histamine release from mast cells, e.g. cromoglycin and intal.
(21) Substances, reducing the Cl-concentration of the extracellular fluid (ECP).
(22) Substances, increasing the ECF-concentration of HCO$_3$-ions. According to the invention, a Ca-overload blocker, especially cinnarizin (component I) should be combined with an antagonist of β-adrenoceptor, histamine-H2-receptor and/or A2-purinergic receptor, especially propranolol (component II). In addition, some selected preparations should be listed which can be used in combination with 1, 2 or more other substances (A+B, A+C ..., B+C, B+D ..., A+B+C, ABD ...). They have a special advantage to represent—as single substances—preparations which can be directly used clinically. They can be combined -as single or as complex preparations- with BRMs.
1 Ca-antagonists (objective: prevention of the intracellular Ca-over-load which results in the deblockade of guanylate cyclase and 5-lipcxygenase and in the inhibition of CaM (calcium modulin)-mediated activation of Ca-ATPase and adenylate cyclase).
1.1 based on nifedipin: adalate (26.071) or aprical 5/–10/– retard (26.072), or bayotensin/–mite (26.075)
1.2 based on verapamil: azuparnil 40/–80/–120 (26.073) or dignover 40/–80 (2.081) or drostreakard 40/–80/–120 (26.083) or verapamil-ratiopharm (26.108)
1.3 based on cinnarizin: cinnarizin-ratiopharm (36.035) or cinnarizin Siegfried (36.036) or cinnarizin R.A.N. 36.034) or cinnacet (36.033) or cerepae (36.032).
2 β-blockers (Objective: inhibition of the cAMP-increasing sub-receptors for catecholamin, PGE1/PGE2 and histamine (H2-R)
2.1 based on acetolol: neptal 400 (26.036) or prent 400 (26.040)
2.2 based on metoprolol: lopresor/–mite (26.035)
2.3 based on propranolol: indobloc 10/40/80 (26.032) or efectolol 10/40/80 (26.024) or elbrol 40 (elbrol 80) 26.027)
3 combination drugs: Ca-antagonists plus β-blockers: beloif (26.070) or tredalat (16.132) or nif-ten 50 (16.131)
4 non-steroidal antiflogistics/antirhumatics (inhibitors of cyclooxygenase/prostaglandin-synthetase)
4.1 based on diclofenac: diclofenac-Wolff-25/50 (05.142) or diclo-OPT 50, 100 retard (05.143) or diclophlogent (05.144)
4.2 based on ibuprofen: dolgit 200/400/SL (05.149) or ibuphlogent 200/–400 (05.161)
4.3 based on indometacin: indo Tablinen (05.170) or indomat retard-rqatiopharm 75 (05.167) or amuno/retard (MSD) (05.129)
4.4 based on ketoprofen: alrheumun (05.128)
4.5 based on acetylsalicylic acid: spelt (05.122) or solpyron (05.121) or gepan/mite (05.117)
5 drugs, affecting the intracellular pH$_i$ (objective: impact on intracellular pH, K- and Na-ion, as well as on the HCO$_3$/Cl$^-$-ratio and herewith on the deblockade of hyper- or persistently activated immunocompetent cells, primarily macrophages)
   (a) hanooxygen (03.007) or gelum oral -rd (03.006(b)) acidovert (03.005) or acetolyt (03.001) or nephrotrans (03.004) or NaHCO$_3$ 1g (03.003)
   (c) histinorm (05.210)
6 drugs, correcting the redox-potential (NAD(P)H$_2$/NAD(P) and GSH/GSSG)
6.1 drugs, improving the mercaptyl-/thionyl-, sulflhydryl-/disulfide-ratio
   (a) acetyl cysteine (23.119) or acetylcystein-ratiopharm 100/200 (23.120)
   (b) metalcaptase 150/–300 (05.201) or trolovol (05.206)
6.2 reducing drugs: cebion (83.099) or cedoxon Cassis (83.100) or cetebe (83.102) or resochin (05.203) or quensyl (05.202) or tauredon (10/20/50). The first two drugs are recommended especially for their oral administration.
7 gold-based drugs (contribute—like chloroquine—to the stabilization of hyperactivated macrophages): ridaura (05.204) (oral) or aureostan 10/25/50/100 (05.199)
9 methylxanthines (e.g. theophylline) (objective: stabilization of the increased cGMP-level following the corrector of the cAMP/cGMP-ratio; methyl-xanthines inhibit not only the cAMP-phosphodiesterase but also the cGMP-PDE): theophyllin retard-ratiopharm 125/250/350/500 (27.082) or theospirex (27.084)
10 antidiabetics (objective: mimicking of the insulin activity or antagonization of the glycolysis- and TCC-inhibiting and gluconeogenase-stimulating activity of glucagon)
10.1 based on biguanidine (metformine): glucophage retard/–mite (11.070)
10.2 based on tolbutamide: artosin 1,0 (11.037) or rastinon-Hoechst (11.065) or tolbutamide 0,5 g/lg (11.067)
10.3 based on glibenclamide: azuglucon –3,5/–1,75 (11.038) or diamicron (11.041) or glucononn 1,75/3,5 (11.051)
10.4 based on glisoxepid: pro-diaban (11.064)
11 guanylate cyclase (cGMP)-stimulating drugs
11.1 based on isosorbid-dinitrate: coleb 20/–40 (54.044) or dignonitrat 40/–60/–100 (54.049)

11.2 based on isosorbid-mononitrate: conpin 20/–40 (54.054) or coragin 20/60 (54.046)
11.3 based on glycerol-trinitrate: nitroglycerin retard-ratiopharm (54.023). An alternative is the sydnonimin-derivative molsidomine (e.g. molsidomine 1/2/4 from ct/Berlin). The working mechanism on the cellular level corresponds to that of org. nitrates; In both cases, the activity of guanylate cyclase and herewith the intracellular cGMP-level is increased.
12 inhibitors of xanthin-oxidase (XOD), with the aim to depress the generation of oxygen radicals (see point (5)): allopurinol 300 Stada (43.007) or allopurinol Dorsch (43.008) or allopurinol-retard Woelm (43.011)
13 some K-saving diuretics (due to K-retard-effect or indirectly due to the stimulation of the $H^+/K^+$-antiport and herewith the pHi-rise).
13.1 based on aldosteron-antagonist spironolacton: spironolacton-ratiopharm 50/–100 (02.016)
13.2 based on triemteren: jatropur (35.060)
13.3 based on amiloride: amiloride per se or in combination with hydrochlorothiazide as amilorid comp.-ratiopharm (35.063)
14 carboanhydrase-blocker, e.g. acetazolamide (due to the impact on the pHi, on the glycolysis, gluconeogenesis and TCC/Krebs (citrate) cycle, as well as due to the depression of the glycolysis inhibiting FPK/fructose phosphate kinase ): diamox retard (67.151) or diamox (39.006)
15 oxygen carriers (objective: an improved $O_2$-transport to the hypoxic inflammatory tissue): oxoferin or TCDO (tetrachlorodekaoxid). The same or a better effect can be achieved with an oxygen therapy. Oxoferin and TCDO can be combined with ascorbate, succinate and/or fumarate.
16 parathormone-antagonizing drugs (PTH acts via adenylate cyclase and cAMP immunosuppressive, like e.g. glucagon, histamine (via H2-receptor), adenosine, PGE2, noradrenaline (via $\beta 1$-adrenoceptor), adrenaline and isoproterenol (via $\beta 2$-adrenoceptor). The macrophages express receptors for (a) insulin (b) glucagon (c) histamine (d) serotonine (e) parathormone (f) calcitonine (g) somatotropine (h) somatostatine (i) PGE2 (j) cAMP (k) $\beta$-adrenoceptor (l) neuropeptides (endorphine) (m) arginin-vasopressin, and (n) transferrin.
16.1 based on etidronacid :diphos (65.005)
16.2 based on clodronacid: ostac (65.007)
17 serene-compounds (objective: ROI-neutralization, stimulation of glutathione-peroxidase)
17.1 based on Na-selenite-pentabydrat: selenase (GN-Pharm)
17.2 based on ebselen
18 Li-compounds (objective: increase of cytoplasmic pHi)
18.1 based on Li-aspartate: Lithium-aspartat-Dragees 120 (70.235)
18.2 based on Li-orotate: Lithium-orotat Tabl. (70.237)
18.3 based on Li-carbonate: hypnorex retard (70.234)
18.4 based on Li-sulfate: Lithium-duriles (70.236)
19 some essential precursors, needed during switching from catabolic to anabolic function: 19.1. L-glutarnine 19.2. ribose 19.3. creatin(in) 19.4. ATP(ADP,AMP) and/or GTP (GDP, GMP, guanin) 19.5. unsaturated fatty acids+ascorbic acid 19.6. EPL 19.7. vanadin-compounds 19.8. glutathion 19.9. folic acid The best combinations are 1+2; 1 or 3+5; 1 or 3+6; 1 or 3+5+6 and 5+6.

Especially recommendable are: in the group 1 1.3., in the group 5 hanooxygen and in the group 6 6.la and/or 6.2. These preferred combinations can be further combined with 4,12, 17 and/or 18,7,8, and 10. An especially preferred combination comprises cinnarizine as component I and propranol as component II. The conventional stimulation e.g. by BRMs can be supported by sub-dosed 11 and/or low-dosed lymphokines (e.g. IL-2, gamma IFN).

The fact that immunocytes react—like other somatic cells—on different, $Ca_i^{2+}$-increasing signals has not been considered up to now.

Therefore, the activation of immunocytes, as well as the in situ/in vivo deblockade of inactivated effector cells (monocytes/macrophages, Ts, NK-cells, K-cells) by alpha-sympathomimetics (e.g. phenylephrine), by Ca-agonists (e.g. Bay K 8644 or CGP 28392) and by $\beta$-receptor blockers (beta-blockers, $\beta$-sympatholytics) is recommended according the invention. These, $Ca_i^{2+}$-increasing compounds can be used alone or combined with each other and/or with immunostimulators and BERMs. They are suitable for the in vitro and in vivo activation and reactivation/deblockade of immunocompetent cells. $\beta$-blockers are able to focus the activity of the physiological agonists noradrenaline (norepinephrine) and adrenaline (epinephrine) on the alpha1- and alpha2-adrenoceptor which favours cell activation (cGMP-rise and cAMP-drop).

According to the invention, a combination of agents with a double impact on $Ca_i^{2+}$-level, i.e. by increasing $Ca^{2+}$-influx and by maintaining the so elevated $Ca_i^{2+}$-level in cytosol through the later blockade of Ca-channels, is of a special interest. Such drug combinations comprise on the one hand alpha-sympathomimetes, Ca-agonists and $\beta$-blockers, and on the other hand Ca-channel blockers (Ca-antagonists, such as nifedipin, verapamil and diltiazem).

Examples of cGMP-increasing compounds are organic nitrites and nitrates, i.e. esters of the nitrous and nitric acid, such as amylnitrite, nitroglycerol, isosorbitnitrate and 5-isosorbitmononitrate, further Na-nitroprusside and parasympathomimetics; the latter can be subdivided in 3 groups: (a) choline ester (e.g. carbachol, bethanechol, metacholin); (b) alkaloids with parasympathomimetic activity (e.g. pilocarpin); (c) inhibitors of choline esterase (reversible inhibitors: physostigmin, neostigmine and pyridostigmin; irreversible inhibitors: fluostigmin and tetrastigmin).

In accordance with the further aspect of the invention, a preparation, consisting of (I) an agent, eliminating the hyperactivated effector cells, and (II) of alloreactive cells with preprogrammed cell death, is recommended. The working mechanism of this preparation is based on the replacement of "handicapped", misprogrammed immunocompetent cells of the patient by the corresponding, in vitro pregenerated (specifically tailored) autologous or homologous/allogeneic immunocompetent cells, a procedure called "microimmunosurgery". This "microimmunosurgery" can be used in patients (a) with cancer (especially solid tumors) (b) with (retro)viral infections, including AIDS, (c) with autoimmune disorders, and (d) with atherosclerosis-based disorders. In other terms, according to the invention, this preparation represents a combination (a) of breaking down (by impairing or eliminating) the resistance of the pathological set of patient's immunocytes, and (b) of reinfusion of the ex vivo pregenerated (specifically tailored) immunocompetent cells. An additional effect is the circumvention of the critical labile interphase by allogeneic and/or autologous immunocompetent cells, pretreated in vitro in a novel way.

The impairment or elimination of the "misprogrammed" (pathologic) immunocompetent cells of the recipient (patient) has been described in all details in the patent applications DE 3812605A1 and PCT/EP89/00403. Here, the novel in visor preparation of immunocompetent cells (a) for the critical labile interphase, and (b) for the reinfusion of a new (healthy) set of specifically tailored immunocompetent cells, is dealt with in detail. The problems, associated with bone marrow transplantations (BMT) are an extreme susceptibility of patients for infections and the unevitable "explosion" of residual tumor cells due to the immunocompromised state of the patients. If the donor-bone marrow cells are not completely depleted of immunocompetent T cells, so called graft-versus-leukemia (GvL)-effect of the non-depleted donor T cells helps to increase the resistance against the infection and the tumor; this advantage is, however, associated with the disadvantage of the graft-versus-host (GvH)-reaction which shows similar fatal complications. With autologous BMT, this GvHR can be prevented. A broader clinical use, e.g. in patients with solid tumors, is however dampened by the extreme immunologic lability of the BMT-conditioned patients and the herewith associated enormous costs (ca. 160.000 dollars/patient).

Both problems, the GvHR in allogeneic system and the extreme immunological instability, associated with extreme costs, both in autologous and allogeneic BMT, can be solved by the $2^{nd}$ variant of the preparation according to the invention, implicating a novel in vitro premanipulation of allogeneic immunocompetent cells. In this way, both the infection and the tolerance-reinduction against the inevitable residual tumor cells in the critical phase, following the removal of primary tumor can be prevented. In autologous EMT, the patient benefits from the "inner immunological stability", which minimizes the outer, extremely expensive sterility measures. This opens the ways to the introduction of BMT in patients with solid tumors. A further advantage is the replacement of the patient-compromising whole-body-irradiation and/or high-dose chemotherapy by a selective depletion of immunocompetent T cells by different Mabs and Mab-based immunoconjugates. This improvement opens new ways for BMT, both in patients with solid tumors and in those, suffering from autoimmune disorders.

According to the invention, the preparation is suitable for a therapeutic procedure, consisting of 3 phases:

(a) In the phase I, the "misprogrammed" immunocompetent cells are eliminated by whole-body-irradiation, by high-dose chemotherapy, by specific Mabs (or corresponding immunotoxins), directed against T cells or their subpopulations (Ts in tumor patients, Tac-$R^+$-cells in autoimmune disorders).

(b) In the phase II, the in vitro premanipulated, specifically tailored immunocompetent cells are injected into the patient, to confer on the patient immunocompetence in the critical, labile interphase.

(c) In the phase III, the patient is injected by ex vivo pregenerated effector cells (CTLs, TILs, LAKs in the case of tumor patients and autoantigen-specific Ts in patients with autoimmune disorders).

Since the phase I is subject of the patent application PCT/EP89/00403 (author: P. Leskovar), only phase II and III will be described here.

The effector cells, needed for the phase II are generated in vitro as follows:

(a) Allogeneic (i.e. donor-) T cells/lymphocytes are cultured first in an isoleucine- or serum free medium to synchronize their cell cycle. Then, isoleucine or serum, respectively, is added and following progression in cell cycle ($G_1 \ldots S \ldots G_2$-phase), the cells are treated by mitomycin C. The mitomycin-concentration is adjusted in the way to allow a 2–5 cell division before cells die (e.g. 1–5 mg/$10^6$ cells). Instead of isoleucin or serum, other essential cell substrates can be used for the cell cycle arrest. Similarly, mitomycin C can be replaced by different mitomycinC-homologs, such as BMV 25282 and BMY 25067, as well as by other DNA-damaging, RNA-sparing substances, such as inhibitors of DNA-polymerase, DNA crosslinking cytotoxic agents and irradiation.

After 12–24 hrs, ideally 18 hrs of incubation with mitomycin C (or other compounds, damaging DNA in a reversible or irreversible way), the allogeneic (donor-) T cells are resuspended in a fresh medium.

To improve the in vitro activation, donor lymphocytes of the bone marrow and/or peripheral blood can be preincubated in a kind of one-way-MLC/MLR with the recipient lymphocytes (favorably with T-depleted or preselected MHC II-positive B cells and/or adherent cells).

This preincubation occurs in isoleucin- or serum free medium; the recipient MHC II-positive cells (B cells) have to be, however, pretreated by mitomycin C or irradiation so that they stay metabolically active but unable to proliferate. During the later mitomycin C-treatment of allogeneic (donor-)lymphocytes (T cells), they get an additional dose of cytotoxic agent, leading to their selective death. The so premanipulated donor cells are activated during the contact with patient's MHC II-positive cells (B cells, monocytes/macrophages, activated T cells), following their infusion into the patient; they secrete IL2 and other cytokines which are reduced or absent in immunoincompetent recipients (due to the lack of mature helper T cells.)

These donor cells can, however, not induce the fatal GvHR or GvHD, as they are "preprogrammed" and die after few cell divisions.

(b) By an alternative procedure donor's mitomycin C-pretreated PBMs(without bone marrow) are injected in the first phase, and donor's T-depleted bone marrow is post-transfused in the second phase. The donor T cells, pretreated in this way, can be replaced or combined with allogeneic (donor-) LAK cells.

Normally, only autologous LAK cells are used therapeutically.

According to the invention, allogeneic (donor-) instead of or in addition to autologous LAK cells should be used therapeutically. The GvHD-complication is not a problem, because the LAK cells consist of up to 90% activated NK cells and of up to 10% non-MHC-restricted $CD3^+$ (T) cells. The T subpopulations which are responsible for the alloreaction and GvHD, cannot survive during the LAK-generation in vitro, due to the lack of antigen (i.e. alloantigen of recipient MHC II-positive cells). T cells can, however, be depleted in vitro by specific Mabs or immunotoxins for reasons of an additional security. Alternatively, L AIC cells can be pretreated in vitro by mitomycin C (or other DNA-damaging substances), as described above.

(c) If for unknown reasons GvHR or GvHD are observed, so a novel strategy can prevent these complications and the GvHD-establishment in general, according to the invention. The principle is the in vitro generation of alloreactive T cells (a) from recipient or (b) from a third person (second donor), directed against donor cells by means of the MLC/MLR-technique.

The donor (first donor) cells have to be pretreated by proliferation-preventing mitomycin C-doses in order to be able to act as stimulator cells in the MLC.

The responder cells (from recipient or $2^{nd}$ donor) are thereafter treated by mitomycin C (or other DNA-damaging substances) in a way, allowing the cells to divide for 2–5 times before they die.

To increase further the efficiency, the autoaggressive subpopulation of patient T cells can be preeliminated by immunotoxins, consisting of cytotoxin (e.g. abrin, ricin, doxorubicin, $^{131}$I-radionuclid) plus IL-2 or anti-Tac/II-2-R-Mab.

According to the invention, the so pretreated effector cells can be frozen, similar to the effector cells with restricted lifespan, described under (a),(b) and (c), in a medium, containing 8–5% DMSO and PVP or PEG of different concentration and mol weight (patent application DE 3812605 A1 and PCT/EP89/00403).

The addition of PVP and/or PEG improves the viability and preserves-in contrast to the sole DMSO-addition-the preactivated state of cryopreserved effector cells. In this way, a repeated infusion of effector cells into the recipient became possible.

An additional improvement is the separation of donor adherent cells (macrophages/monocytes) before the mitomycin C-treatment, followed by their later readdition to the mitomycin C-pretreated effector cells (T cells, lymphocytes) and infusion into the patient.

Mitomycin C can be combined with interferon (alpha, beta, gamma), TNFalpha, DMSO, vitamin A and E, as well as the (re)differentiation substances, such as butyrate.

The following procedure is also especially preferred: Patient's lymphocytes can be clonally expanded in vitro into tumoricidal CTLs and plasma cells by mitogenic lectins (PHA,ConA) and mitogenic antibodies (anti-CD3/Ti, anti-CD2/T11). This in vitro postexpansion comprises only the blastogenically pretransformed T and B clones, i.e. memory T and B cells. Since tumor patients have a persistent contact with tumor cells and AIDS/ARC/LAS-patients with HIV and opportunistic infections, respectively, their blood contains corresponding memory cells. Depending on the cell structure conditions, these memory cells can be directed toward CTLs (CD8$^+$, and CD4$^+$) or Ts cells; this opens new ways for their therapeutic use (a) in tumor- and AIDS-patients, and (b) in patients with autoimmune disorders.

If the resistance (immunocompetence) of the patient is temporarily down-regulated, the infusion of in vitro clonally postexpanded patient's lymphocytes (T cells) can have an essential impact on the disease development. The expansion of CTLs can be achieved e.g. by the PHA-treatment for 3–6 days. The autotolerant Ts cells, necessary for the therapy of autoimmune disorders, can be generated e.g. by the treatment with PWM for 7 days or with the PHA for 3–4 weeks. The CD8$^+$-rise is accompanied by a CD4$^+$-drop. These Ts cells can be cultured for more than 6 months under following conditions: 2 times weekly, IL2 is added to the medium and cells are restimulated by feeder cells and PHA every 2 weeks. These cells suppress the proliferation of autologous and heterologous CD4$^+$ T cells when stimulated by PWM, OKT3 or tetanus toxoid.

Alternatively, Ts cells can be generated in vitro in the presence of PGE2, anti-IL1, anti-IL2, anti-IL4, cyclosporinA, rapamycin and/or FK506.

The Ts-depleted cytotoxic effector cells, needed in the tumor and AIDS/ARC-therapy, can alternatively be enriched by the elimination of CD8$^+$ cells (by means of Mabs or immunotoxins). The spared CD4$^+$ T cells are able to induce in vivo new CTLs; this process is accelerated by anti-PGE2, anti-lipocortin/macrocortin and anti-TGF-beta. In AIDS/ARC/LAS-patients, it is advantageous to preimmunize the patient with the lysate of opportunistic infections, before the in vitro expansion of memory cells; alternatively, a healthy donor can be preimmunized (a) with a viral antigen (8p 120) and (b) with mentioned lysate.

The so generated clonally postexpanded allogeneic memory cells (T and B cells) can be treated by mitomycin C, washed and injected into the AIDS-patient.

Atherosclerosis and other coronary diseases show an autoimmune genesis (our own experiments, reports of others, e.g. W. Hollander); therefore, the agent(s), based on "microimmunosurgery", are able to replace or support the "conventional" treatment.

According to the invention, hyperactivated B or T or both B and T cells of atherosclerotic patients are depleted/inactivated by means of "microimmunosurgery". It is advantageous to replace them by the in vitro pregenerated Ts fraction. These Ts cells can be generated by a simple, 3–5 week incubation of patient's PBMs with ConA or PHA. Alternatively or supportingly, the patient can be treated by special preparations which inactivate the hyperactivated macrophages; they consist of Fab/F(ab')$_2$-subunits (labeling) or immunotoxins (depletion), directed (a) against the (acid-labile and acid-resistant) Fc(gaTnma)-receptor, (b) against the complement receptor (CRT, CR3), (c) against the scavenger/AcLDL-receptor (I and II), (d) against the gamma-interferon-receptor and /or (e) against the LPs/endotoxin-receptor. Alternatively, the biotechnologically synthesized receptor per se or its subunits can be used therapeutically.

In addition, denatured (e.g. heat-denatured) complement subunits (clq, c3b, c3d etc.) or biotechnologically produced defect C-components can be used; they can be combined with antioxidants (vitamin E,A, probucol). The in vivo neutralization of the solubilized ApoB,E- and ApoE-receptor in the patient's plasma, following their quantitative determination in vitro, is also advantageous.

An alternative way comprises a combination (a) with Ca-antagonists/Ca-channel blockers (verapamil, nifedipin, dilthiatem), (b) with cGMP-increasing substances (e.g. Na-nitroprusside, org. nitrates), and (c) with phi-raising substances. In this way, the replacement of "wrongly programmed" (hyperactivated) macrophages by "fresh" monocytes should take place.

The protracted or repeated microimmunosurgery includes the prevention of neutralizing antibodies against xenogeneic (mostly murine) Mabs and Mab-based immunoconjugates by substances, specified in the patent application PCT/EP89/00403, as well as by some procedures, described here:

(1) Prevention of neutralizing antibodies by the pretreatment of recipient with Mabs which are coupled as a kind of hapten to a tolerogen as carrier. Examples of such tolerogenic carriers are polyethyleneglycol (PEG), polyvinylpyrrolidone (PVP) and different copolymers of D-amino acids (e.g. D-glutamine-lysine, shortly D-GL).

(2) The same principle (like under (1)) can be applied to different immunoconjugates, e.g. conjugates of Mabs (directed against tumor cells, viral/bacterial infections, leukocyte-subpopulations) with (a) cytotoxins, such as ricin or abrin, (b) with cytotoxic agents, such as doxorubicin, (c) with radionuclids, such as $^{131}$I, and (d) with target cells-starving enzymes, such as arginase, asparaginase etc. A two-step-administration (first sub-immunogenic, then immunogenic dose), can additionally potentiate the effect.

(3) Neutralizing antibodies against xenogeneic (murine) proteins (e.g.Mabs) can be prevented also by strictly monomeric, molecular-dispersed structure of these xenogeneic proteins, which can be achieved by their pretreatment (a) by mercaptoethanol (b) by glutathione (c) by N-acetyl-cysteine (d) by penicillamine D (e) by other substances which support the disulfide-to-thioVsulfhydril-interconversion, as well as by 6M-urea and guanidine-hydrochloride.

(4) Prevention of neutralizing antibodies by a direct in vivo use of Mab-producing plasma cells, which induce a low-zone tolerance against xenogeneic proteins by secreting strictly monomeric Mabs; these are not xenogenized by in vitro manipulation.

(5) Prevention of neutralizing antibodies by the direct in vivo use of Mab-secreting hybridoma cells, which were pretreated in vitro by mitomycin C and/or other DNA-crosslinking cytotoxic agents (restricted lifespan, 2–5 cell divisions only).

(6) Prevention of neutralizing antibodies by aggregate-preventing substances, e.g. protein-solubilizing tensids (e.g. salts of higher fatty acids, Iysolecithin) at extremely low concentrations).

As next, some further details to this invention will be dealt with:

The hyperactivated, suppressive macrophages can be inactivated as follows:
(a) by antioxydants (b) by inhibitors of enzymes, involved in ROI-synthesis (c) by PAF-blockers (d) by PLAZ/PLC-inhibitors and/or (e) by Ca-channel blockers/Ca-antagonists. In the $2^{nd}$ phase, the recruitment of new macrophages from monocytes is foreseen.

The in vitro generation of blastogenically pretransformed (memory) cells can be accelerated if patient's PBMs are first treated by anti-CD8- and/or anti-CD3-Mabs plus complement or by corresponding immunotoxins. This leads to a partial Ts-depletion and should be followed by the treatment with mitogens (lectins or mitogenic Mabs).

In patients with autoimmune disorders, the addition of Ts-stimulating substances (anti-HLA-DR-Mab, anti-LFA-1beta-Mab, cyclosporina, corticosteroids, FK 506, rapamycin, ConA) and in patients, suffering of cancer or AIDS (and other viral diseases), the addition of Tc(CTL)-promoting substances (anti-HLA-DQ-Mab, anti-LFA-alpha-Mab, cyclooxygenase-inhibitors such as aspirin, indomethacin, anti-PGE-Mab etc.) is recommended. The preferred generation of Tc instead of Ts cells can be observed in vitro also when adherent cells are removed. This technique is based on the effect of ex vivo specifically tailored effector cells on the disease regression; the patient's immunologic resistance has to be temporarily reduced by anti-CD8-Mab and/or anti-CD3-Mab (in the case of tumor- and AIDS-patients) and by anti-CD3-Mab (in patients with autoimmune disorders): The therapeutic efficiency in tumor patients is further increased if patient's tumor cells are incubated in the presence of gamma-interferon, TNFalpha and/or 5-HETE in order to induce MHC I and/or MHC II-postexpression on the cells and are then reinjected along with patient's specifically tailored, in vitro postexpanded memory cells.

A further increase in efficiency can be achieved by the confusion of patient's glutaraldehyde-pretreated macrophages which have been preincubated with tumor antigen. An additional advantage is the confusion of patient's inactivated (preirradiated or glutaraldehyde-pretreated) leukocytes (PBMs) which results in the induction of antiidiotypes, directed against patient's Ts cells. The infusion of hybridoma cells, based on patient's tumor cells and MHC II-positive autologous and homologous cells is advantageous, as well.

The above discussed LAK/TIL-techniques can be further improved by adding mitomycin C-pretreated allogeneic (donor) T cells to LAK or TIL cells. This increases the number of lymphokine-secreting cells which is especially important for the TIL-technique.

These premanipulated allogeneic cells are able to play a similar positive role in bone marrow recipients. The preexpanded allogeneic cells can be used also in the treatment of autoimmune disorders and GvHD, if they are pretreated by DNA-damaging agents. The RES-elimination (99%) of LAK and TIL cells due to their "xenogenization" during the ex vivo manipulation can be reduced, according to the invention, by addition of alpha2-macroglobulin, antitrypsin and/or cortisone to the medium.

A variant of the described procedure renders the externally controlled in vivo production (a) of cytokines (e.g. TNFalpha, IL-1, IL-2, IL4, IL-6, IL-3, G-CSF, M-CSF,GM-CSF), (b) of hormones (e.g. insulin, parathormone etc.), and (c) of other physiologically important cell factors possible. The principle is the transfection of donor specific recipient T cells by corresponding, these cytokines or hormones encoding genes; the preselection of alloreactive, donor-specific recipient T cells can be achieved by a (repeated) one-way-MLC (stimulator cells: donor-PBMs; responder cells: recipient-PBMs).

After the reinfusion of the transfected recipient T cells, these can be repeatedly reactivated in vivo to secrete cytokines or hormones by injecting i.v. inactivated (mitomycin C-pretreated or preirradiated) donor-PBMs. After the in vitro pregeneration of autologous, alloreactive T memory cells, directed against donor A, donor B, donor C etc., different functions can be transfected donor-dependently into these recipient memory cells and "recalled" in vivo, following the reinjection of these manipulated autologous cells into the recipient. By the intratumoral injection of these cells, the effect can be localized to the tumor tissue. A similar in vivo "switching on" of the desired function can be achieved by the following procedure: the recipient T cells are first primed in vivo by a model antigen and then clonally postexpanded in vitro in the presence of the same antigen. In the next step, these cells are transfected by the gene of interest, e.g. cytokine- or hormone encoding gene(s) and reinjected into the recipient, favorably after the temporary depletion of recipient's immunocompetent cells. Later restimulation of the recipient by the same model antigen "turns on" the desired ("transfected") cell function. Representatives of such antigens are tuberculin and other antigens, used in cutaneous tests, as well as haptens (DNCB, DIBM, DNBS, TNBS etc.).

Instead of the above described alloantigens and model antigens, low-dose allergens can be used.

This externally controlled in vivo secretion of cytokines is of special interest in the therapy of strongly immunocompromised patients (AIDS/ARC/LAS-patients, patients with advanced cancer, recipients of bone marrow grafts).

The above discussed transplantation (a) of organs (b) of bone marrow and (c) of mitomycin C-pretreated, hormones (e.g. insulin) and cytokines-secreting allogeneic or xenogeneic cells and hybridomas can be essentially improved by the following procedure: First, the immune resistance of the recipient must be temporarily down-regulated ("broken") by specific antibodies (anti-panT- or anti-CD8-Mabs) or Mab-based immunotoxins. Then, the in vitro pregenerated suppressor T cells (Ts) (see above !) are reinjected, immediately before the transplantation. The main advantage over the "conventional" grafts is that here -in contrast to the "conventional" grafts- the recipient is not confronted "unexperienced" with the MHC II-positive donor cells (bone marrow macrophages and B cells, as well as "passenger lymphocytes" in organ grafts) but preinjected by allotolerant Ts cells; these donor-specific Ts-memory cells direct the CD4/CD8-double positive precursor cells (inducer/transducer suppressor cells) towards the Ts-effector cells before the alloreactive Tc/CTL cells predominate. This seemingly minimal deviation in the procedure can decide about the survival of organ- and bone marrow recipients.

The tolerance against the organ or bone marrow graft, as well as against the hormone (e.g. insulin) or cytokine-producing allogeneic cells can be induced also in the following way: Alloreactive donor-specific recipient T cells are selected and expanded in vitro by means of MLC (responder cells: recipient PBMs, stimulator cells: donor PBMs). The repeated MLC results in a 95% enrichment of these alloreactive T cells. The next step is the inactivation of recipient's donor-specific alloreactive PBMs or T cells by irradiation or mitomycin C: Before they are injected into the recipient, the latter must be temporarily rendered immunoincompetent (by anti-CD3- or anti-CD1- or anti-CD8-Mab). The principle here is the induction of anti-idiotypes in the recipient (in vivo), before this encounters MHC II-positive donor cells (bone marrow cells or "passenger lymphocytes"). Therefore, this induction of anti-idiotypes has to be carried out several days before the real transplantation.

Problems, associated with the transplantation, such as immune suppression or susceptibility for infection can be reduced by the co-infusion of in vitro inactivated allogeneic (donor) MHC II-positive cells (B cells, macrophages), along with the allotolerant Ts cells. These MHC II-positive cells can be pregenerated in vitro by a kind of MLC (responder cells: recipient-PBMs, stimulator cells: donor-PBMs), frozen and during or after the transplantation repeatedly reinjected into the recipient.

The precursor cells can be directed toward Ts cells by the addition of anti-HLA-DR- and/or anti-LFA-lbeta-Mabs. In contrast, the generation of Tc/CTLs can be induced in the presence of anti-HLA-DQ- and/or anti-LFA-1alpha-Mabs. The rise of MHC II-positive APCs ("passenger lymphocytes"), which is critical for the graft failure, can be prevented by the addition of anti-HLA-DR-Mab or the corresponding Fab/F(ab')$_2$-subunit and/or Ca-channel blocker (verapamil,nifedipin, dilthiazem).

A further improvement of the above discussed LAK/TIL-technique can be achieved (a) by co-infusion of mitomycin C- preinactivated allogeneic, MHC II-positive cells (B cells, adherent cells), and (b) by the addition of sub-dosed corticosteroids and/or serum proteinase inhibitors (alpha2-macroglobulin or alpha1-antitrypsin) to the medium during LAK or TIL generation. The so modified culture medium prevents the in vitro xenogenization of LAK and TIL cells and herewith their early RES-elimination in vivo.

The activation of tumoricidal/virucidal effector cells can be achieved also through a controlled treatment of these effector cells (NK cells, T cells, macrophages) (a) by fusogenic substances in sub-fusogenic concentrations (e.g. PEG, PVP), further (b) by electrofusion under sub-fusogenic conditions (1000–5000 kHz; 10–150V/cm$^2$) and/or (c) by proteolytic enzymes and lipases.

The above described hybridomas can be used, according to the invention, also to stabilize and to establish herewith new cell lines which normally wouldn't survive in vitro.

An improved localization of the above described, transfected, cytokines or hormones secreting T cells can be achieved by "arming" of these transfected cells with bifunctional Mabs which recognize these both transfected cells and the tumor cells.

In order to induce a kind of allergic reaction against tumor cells, the "conventional" anti-tumor-Mabs which are normally of the IgG-isotype, can be combined with anti-tumor-Mabs of the IgE-isotype. The latter can be produced in vitro by the "isotype switching" of plasma cells from the IgG- to the IgE-production; the process of "isotype switching" can be induced by addition of anti-gamma interferon and anti-IL2-Mab, as well as IL3, IL4 and IL5 to the medium. A simultaneous addition of anti-CD8-Mab is advantageous. In the case of anti-tumor-IgGs the immortalization (hybridoma formation) is carried out before and in the case of anti-tumor-IgEs after the "isotype switching" of plasma cells. Alternatively, anti-tumor-Mabs of the IgE-isotype can be constructed by the conjugation of xenogeneic (murine) anti-tumor-Mabs (more precisely: Fab/F(ab')$_2$-subunits) with human Fc-subunits.

According to a further variant, a direct in vivo use of hybridoma cells, produced before (IgG) or after (IgE) the "isotype switching" is recommended; these hybridoma cells have to be pretreated by DNA-damaging, RNA-sparing agents (e.g. MMS, mitomycin C etc.)

In a further variant, anti-gamma-interferon plus IL4 (IL-3, IL-5) are directly injected into the patient; herewith the activity of $T_{H2}$ cells is increased and that Of $T_{H1}$ cells depressed which leads to an early "isotype-switching".

The next strategy is the replacement of the immortalizing (transformed) partner cell (e.g. NS-1) in the hybridoma and quadroma cell by MHC II/HLA-DR-positive (allogeneic) cell. In this way, the hybridoma and quadroma cells can be externally switched on and off. The new procedure is based (a) on the in vitro pregeneration of alloreactive T cells of the recipient, directed against the donor A and further donors (donor B. donor C etc.) by means of the (repeated) MLC, (b) on the fusion of preselected alloreactive memory-T-cells with partner cells which are used for "conventional" hybridizations (e.g. anti-tumor-Mab producing plasma cells), as well as (c) on the reinfusion of the so generated hybridoma cells into the temporarily immunocompetent recipient. These hybridoma cells which are well tolerated, as they are fully (in the case of human autologous plasma cells) or partially autologous (in the case of murine plasma cells), can be later reactivated repeatedly by the injection of donor-lymphocytes.

A kind of tumor-directed "autoreactivity" can be achieved as follows: tumor cells of the patient are stimulated in vitro by gamma-interferon (TNFalpha, 5HETE) to post-express MHC II (and MHC I) on the cell surface. Alternatively, tumor cells can be fused (a) with autologous or (b) allogeneic, MHC II-positive cells and washed thoroughly.

A further xenogenization of patient's tumor cells can be achieved by the fusion with LPS-containing gram-negative bacteria and/or yeast cells. After their inactivation, these manipulated tumor cells are injected into the patient who has to be rendered immunoincompetent temporarily (by injection of anti-CD3-, anti-CD1, anti-CD2- or anti-CD8-Mab). In this way, the autoaggression against tumor cells can be induced.

Hybridoma cells, arising from patient's tumor cells and MHC II-positive allogeneic cells (e.g. allogeneic B cells) are able to accelerate the induction of the autoaggressive reaction against tumor cells if they are combined with (repeated) injection of inactivated PBMs from that donor whose MHC II-positive cells were used as partner cells for the hybridization with patient's tumor cells (see above).

The same techniques can also be used for the improvement of conventional vaccines (e.g. against bacterial and (retro)viral infections, including HIV). So, the efficiency of conventional vaccines is essentially increased if they are combined with anti-CD8-Mabs (or the corresponding immunotoxins) and/or with complete and incomplete (Freud)-adjuvant. It is also advantageous to combine the 1$^{st}$ vaccination ("priming") but not the 2nd vaccination ("boosting") with anti-B-cell-Mabs (e.g. anti-CD19-, anti-20-, anti-CD21-, anti-CD22-Mab). The in vitro preformed immune complexes, composed of pathogen and anti-pathogen (IgM-isotype) with or without bound complement or complement-subunits (clq, c3b/c3d etc) can also be promising. Alternatively, the efficacy of the vaccine can be improved by IgE-inducing IL3, IL4, IL5 and anti-gamma-interferon.

The above discussed GvHD can be prevented also by autologous PBMs which have been also preactivated by a repeated MLC. In this MLC, the responder cells are autologous (recipient) PBMs and stimulator cells the allogeneic (donor) PBMs; the latter have to be preirradiated or mitomycin C-pretreated. The repeated co-incubation of donor- and recipient-PBMs leads to the generation of highly efficient alloreactive memory cells which are able to eliminate the GvHD-causing donor-T-cells.

The autologous BMT can be improved: (a) by preelimination of suppressor-T-cells in vitro, e.g. by anti-CD8-Mabs or corresponding immunotoxins, (b) by in vitro preactivation of effector cells, (c) by addition of autologous and/or allogeneic LAK-cells (the allogeneic LAK-cells can, but need not be predepleted of CD3-positive cells), (d) by addition of autologous, $CD8^+$-depleted PBMs to the autologous bone marrow cells (the PBMs should be preactivated in a tumor-specific way), as well as (e) by the addition of allogeneic, favorably preactivated allogeneic PBMs which have to be pretreated by mitomycin C or other DNA-damaging and RNA-sparing substances in order to confer to the alloreactive subpopulation a restricted lifespan.

According to the invention, the stepwise addition of increasing doses of anti-CD8- or anti-CD3-Mab plus complement (or of corresponding immunotoxins) to the patient's PBMs allows the determination of the critical T cell number/ml which directs the immune response from suppression to stimulation (deblockade) of T4 and B memory cells. The so premanipulated autologous PBMs mimic the favorable clinical situation, when autologous marrow cells are collected during remission (PR or CR) and not during relapse.

This technique is recommended especially for patients with solid tumors, as well as for AIDS/ARC/LAS-patients.

The above mentioned LAK cells show the special advantage that they cannot be contaminated with (tumor-specific) Ts cells; a further advantage is the lymphokine-production by autologous T cells, directed against allogeneic LAK-cells, which is especially important for immunocompromized recipients. The LAK-cells of one or more persons could be frozen and used for different patients, especially after an anti-CD3-pretreatment ("standardized LAK-cells").

As next, some additional improvements of the techniques described above should be quoted: So, the restricted lifespan of hybridoma cells can be achieved by the change of the ratio of partner cells during hybridization, instead of the treatment of hybridoma cells with DNA-damaging and RNA-sparing agents. It concerns the chemical (PEG) and viral (SV-40) fusion, as well as the electrofusion.

If the ratio of partner cells which contribute to the immortalization of hybridoma cells in comparison to those which contribute the desired function is reduced from "classical" 1:1 to 1:2; 1:3; 1:4; 1:51: . . . 1:10, a controlled longevity of hybridoma constructs can be achieved, similar to that, achievable by low-dose mitomycin C. By an early fusion of instable cell lines, which don't grow ex vivo, with transformed cells, these cells can be "stabilized" and are able to survive in vitro.

According to the invention, the fusion of lymphokine and hormone-producing cells with transformed cells, followed by the mitomycin C-treatment, opens for the first time the possibility of a direct in vivo implantation of cytokine and hormone-producing cells (e.g. insulin production). The so pretreated secretory cells die after a limited number of cell divisions and can be substituted by a new set of premanipulated cells; this allows an efficient control of the cytokine and hormone level.

The tolerance against such secretory cells can be achieved (a) by the simultaneous treatment with immunosuppressive substances (cytotoxic agents, sub-dosed anti-CD4- or anti-MHC II-Mab), (b) by cell implantation in thymus and/or (c) by "autologization", i.e. by use of autologous partner cells for hybridization. Further comments: In AIDS-patients, the in vitro presensibilization of patient's lymphocytes (T cells) by preirradiated of mitomycin C-pretreated donor-lymphocytes (T cells), followed by the transfection of alloactivated patient's T cells with cytokine or anti-HIV-Ab-producing genes, and reinfusion of the so transfected autologous T cells into the patient is recommended. A part of transfected cells can carry the gene for the IgG-isotype and the other part that for the IgE-isotype. The later "switching on" of the cytokine and antibody-production occurs by the injection of inactivated donor lymphocytes.

According to a simplified version, the patient's T cells in general, not only his donor-specific alloreactive T-subclones can be transfected in vitro with cytokine and/or anti-HIV-antibodies-encoding genes, and reinjected into the patient. Again, the later "switching on" of the in vivo cytokine and antibody production occurs by the injection of donor-lymphocytes; the system works because patient's lymphocytes always contain T cells which are alloreactive against the donor.

In conventional vaccines, the ratio between "positive" (Th andTc/CTL) and "negative" (Ts) memory cells can be increased as follows: (a) In the $2^{nd}$ phase, i.e.4–6 days after the vaccination, the couterregulation of persistently activated macrophages can be delayed by Ca-channel blockers and macrophages-inactivating measures (ROI-inactivating agents, such as retinol, tocopherol or carotinoids, glutathione, ascorbate, radical-scavengers). (b) With anti-HLA-DQ (not DR) and anti-LFA-lalpha (not beta), the (Th+Tc)/Ts-ratio can be positively influenced. (c) A similar effect (increase of the (Th+Tc)/Ts-ratio) can be achieved by anti-lipomodulin/anti-lipocortin/anti-macrocortin-Mabs and/or mellitin. (d) Ba the conjugation of pathogen antigens (viral or bacterial structures) to carriers which are used as components of common vaccines, such as tetanus and diphterytoxoids, tuberculin, inactivated M. tuberculosis and BCG; the efficiency of conventional vaccines can be further increased. (e) an additional improvement is the use of anti-thymosine-alpha7 (not alpha1). (f) The efficiency of vaccines can be also increased by anti-PGE2(E1) and by PGF2alpha. (g) The resistance against pathogenic microbes can be increased as well, if first contact with antigen structures of the pathogen (e.g. gpl20/160 or gp 41 of HIV) occurs via alveolar macrophages which prevents its early contact with Ts cells (as in the case of the i.v. administration). Therefore, the sensibilization by aerosol-spray as the only or at least first step ("priming") is recommended. (h) In the $2^{nd}$ phase of vaccination, i.e. 4–7 days after vaccination, the Ts generation should be prevented by anti-PGE2- and anti-interferon-Mabs. (i) The in vitro preformed IgE.antigen:IgE-complexes are able to activate the IgE-R-expressing cells (macrophages, NCF-A-, ECF-A- and kininprotease-secreting mast cells) in the critical early phase.

Some additional techniques: (a) Tumor patients can be treated by inactivated hybridoma cells, arising from patient's tumor cells and allogeneic (donor) cells of the same origin, i.e. the same organ like tumor. An example are leukemia cells, fusioned by the same lymphocyte-subclass of the healthy donor. (b) The Th(=$T_M$) cells can be stimulated in vivo if the injection of antibodies of the IgM-isotype is followed by the injection of the corresponding antigen. Analogously, the TS(TG) cells can be stimulated in vivo by the successive infusion of IgG and the corresponding antigen. (c) Similarly to the above described "allogeneic switching", autologous lymphocytes can be primed in vitro by a model antigen and the resulting memory cells transfected by cytokine and Mab-encoding genes. After the reinfusion they respond to the resensibilization by the same model antigen. The strongest response show the cutaneous antigens. It is advantageous to use the preexistent memory cells which stem e.g. from previous vaccinations (e.g. tuberculin) or sensibilization (DNCB, DNBB, TNBS). (d) By anti-CD3-, anti-TCR/Ti-, anti-CD2/T11- and other mitogenic Mabs, the memory but not naive T cells can be stimulated to proliferate; in naive/non-primed T cells, the mean distance between membrane antigens of the same structure, e.g. CD3 or Ti is too long to be "bridged" by both Fab-subunits. Therefore, novel antibodies are recommended according to the invention, containing two or more anti-CD3(Ti, CS2 . . . ) -Mabs or their Fab/F(ab')$_2$-subunits, conjugated to different spacer-molecules; this renders a direct crosslinking of CD3-, Ti-, CD2- and other membrane structures possible even on naive Th-cells. In this way, an APC-independent activation of naive Th-cells is possible which can be of relevance in immunosuppressed AIDS and tumor patients.

In order to prevent at the same time the neutralizing antibodies against xenogeneic (murine) Mabs, the use of strong tolerogens, especially polymers/copolymers of D-amino acids, e.g. D-GL, or PEG or heparin or sialic acid-based polymers, is recommended.

The efficacy of the novel type of antibodies can be further increased by their combination with interferon which increases the surface density of structures to be crosslinked.

The tumoricidal and/or virucidal effector cells can be activated in a novel way by conjugating Mabs or their Fab/F(ab')$_2$-subunits, recognizing (a) cytokine receptors or (b) growth factors (EGF, IGF, PDGF etc.) with spacer molecules, e.g. the $CH_2$)n-chain or D-GL. D-polylysine as spacer molecule is of special interest, as it is a tolerogen and as it facilitates—through the positive charge—the approach of the Mab-construct to the target cell. The same is true with the polymers or copolymers of other basic, D-aminoacids. The here described new principle of introducing spacer molecules as carriers of Mabs with the same or different specifity, is also applicable for all simple or combined Mabs, specified in the patent applications PCT/EP ( )/00403 and DE 3812605A1. (e) Since LAK cells consist to 90% of NK cells and to 10l of non-MHC-restricted CD3$^+$-cells and are free of alloreactive, GvH-inducing T cells, the allogeneic LAK cells can be used to circumvent the immunoincompetent phase which is critical for later relapses (a) in bone marrow recipients and (b) in patients, immediately following tumor surgery. LAK cells can be depleted of T cells before their infusion into the patient. LAK cells can be frozen by a special procedure (with PEG/PVP-addition to DMSO), preserving their preactivated state.

*(f) Atherosclerosis seems to be induced by an autoimmune primer, including hyperactivated macrophages. The latter can be depressed (a) by corticosteroids (b) by Ca-antagonists (c) by masking the Fc and CR1/CR3-receptors with Fab/F(ab')$_2$-subunits of the anti-receptor-Mabs (d) by ROI-reducing agents and radical-scavengers, and (e) by anti-CD19(CD20, CD21, CS22)-Mabs (temporary depletion of CIS-producing B-cells). Within the inflammatory tissue, the immunocytes are exposed (a) to hypoxic/anoxic and/or (b) acidic micromilieu. (a) The unfavorable redox-potential in this tissue has to be normalized by $O_2$-carriers (e.g. oxoferin, TCDO=tetrachlorodekaoxid) and/or by other electrone acceptors (e.g. ascorbate, dehydroascorbate, (poly)unsaturated fatty acids). (b) The low pH in the inflammation tissue inhibits immunocompetent cells. By the pH-rise, the $H^+/Na^+$-pump of immunocytes must be relieved. Examples of $pH_i$-raising agents are quaternary bases and their salts (carbonate, citrate, maleate), further TRIZMA (as base or as salt), THAM/tromethamine/trometanol, mono-, di- and triethanolamine, etc. An intracellular pH-rise to 7,3–7,6 is the prerequisite for cell proliferation. The $O_2$-deficit is associated also with prostaglandin instead of leukotrien-synthesis. In order to down-regulate the immunosuppressive effect of hyperactivated macrophages on immunocompetent cells in inflammatory tissue (tumor, persistent infection etc.), the following steps are recommended: (a) treatment by Mabs and immunotoxins, directed against the surface antigens on end differentiated macrophages (x-4, x-11, x-12, x-14, x-15) and against the differentiation antigens on hyperactivated macrophages (b) treatment by cytotoxic substances, encapsulated in liposomes (c) treatment by agents which stabilize the lysosome-membrane in macrophages (e.g. gold preparations such as aurothioglucose, aurothiopolypeptide or Na-aurothiomalate, further antimalaria-agents such as chloroquine and D-penicillamine).

The proteases are able to switch the cell from the suppressor—to the effector function. The GEF (glycosylation enhancing factor), a kallikreinlike kininprotease prevents the GIF (glycosylation inhibition factor)-induced immune suppression; a membrane-associated serine-protease is directly involved in the process of cell activation.

The lipases are able to activate—via lysophosphatide—immunocytes (macrophages, NK-, K-, T-cells). This activation results partly from the mimicking of membrane-associated phospholipases (PLC, PLA2). The effect of mucopolysaccharidase is similar to that of proteases. Therefore, the deblockade of immunocytes by proteases, lipases and mucopolysaccharidases is recommended, both per se or in combination with the above described cell activators.

Interferons, TNFalpha and TGFB switch the cell from proliferation to dedifferentiation. Their pathologically increased levels exert an antiproliferative effect on precursor cells, depressing in this way the recruitment of immunocompetent cells. Such pathologically raised levels of cytokines can be measured in AIDS- and tumor-patients, but also in autoimmune disorders and persistent infections. Therefore, these antiproliferative cytokines should be neutralized by specific Mabs. In tumor- and AIDS-patients, the immune response can be improved by special conjugates, consisting of the Fab/F(ab')$_2$-subunit of tumor- or HIV-specific Mabs of murine origin plus the Fc epsilon-subunit of human origin.

Some membrane-associated immunorelevant structures (e.g. MHC II, MHC I, CD4, CD8, B2m) become immunosuppressive if they are shedded into the plasma. The neutralization of such solubilized membrane structures by specific Mabs helps to prevent their immunosuppressive effect.

A further advantage is the use of anti-HLA-DQ- and anti-LFA-lalpha Mabs.

The following procedure is of special interest:

(a) Tumor patients are first in vivo depleted of the tumor-protecting suppressor T cells (see patent applications DE3812605A1 and PCT 94/EP89/00403.

(b) Patient's tumor cells are treated in vitro by IFN gamma and/or TNF allpha (postexpression of MHC II and MHC I), inactivated by anti-HLA-DQ- and/or anti-LFA-lalpha or their Fab/F(ab')-subunit and reinjected into the patient. Alternatively, the tumor cells can be fusioned (in the presence of PEG) with autologous and/or allogeneic MHC II-positive cells (B cells or macrophages), treated by anti-HLA-DQ- and/or anti-LFA-lalpha-Mab and reinjected into the patient. Both alternative procedures include the immune reactivation of the patient as an important step.

The principle of the here discussed novel tumor therapy is to combine (a) the temporary breaking of resistance of immunocompetent cells with (b) the reinfusion of in vitro pregenerated tumor-specific T cells. It is essential that these cells are memory cells; according to laws of the so-called "restricted" CML (CML to non-MHC-molecules), only the blastogenically pretransformed T cells are able to induce in vitro the response to the (soluble) antigen in question.

The tumor-specific T cells are capable to induce in vivo a kind of autoimmune reaction against the tumor antigen if they are generated as follows:

(a) Patient's lymphocytes (T cells) are postexpanded in vitro polyclonally, e.g. by PHA, then the CD8-positive Ts cells are eliminated e.g. by specific Mabs or immunotoxins, and the residual CD4-positive T cells are reinjected into the patient, along with the memory cells. In vivo, these T4 cells are able to induce the CTLs with specificity for tumor cells. Instead of the $CD8^+$-postdepletion, the inducer-suppressor subpopulation can be inactivated in advance by a 500 Rad-preirradiation.

(b) Alternatively, patient's lymphocytes (T cells) can be co-incubated in vitro with his malignant cells, after these have been induced to post-express the MHC II-antigen.

(c) An interesting further way comprises the reinfusion of patient's lymphocytes (T cells), along with mitomycin C-pretreated patient's macrophages.

The success of organ- and bone marrow transplantation can be essentially improved if the donor organ, more precisely its "passenger lymphocytes". or donor bone marrow cells, respectively, are pretreated in vitro by anti-HLA-DR- and/or anti-LFA-lalpha-Mabs (or their Fab/F(ab')$_2$-subunit).

Alternatively or additionally, the MHC-postexpression on "passenger lymphocytes" can be depressed by Ca-antagonists (e.g. verapamil, nifedipin, diltiazem) or by anti-mitogenic substances (colchicin, domecolcin, gliotoxin). This MHC II- postexpression, following the organ surgery seems to be critical for the later organ rejection. As mentioned above, the bone marrow cryopreservation can be essentially improved by the addition of PEG and/or PVP of dofferent mol weight to DMSO.

An interesting novel approach in tumor therapy is the use of hybridoma cells with restricted lifespan, constructed of tumor-specific immunocytes and mitomycinc-pretreated immortalized partner cells. One variant proposes (a) to fuse the pregenerated immunocytes with myeloma cells which are routinely used for hybridization purpose, and to treat the resulting hybridoma cells with mitomycin C. (b) The other possibility is to fuse the pregenerated immunocytes with mitomycinC-pretreated myeloma partner cells, or(c) to use the commercially available non-transformed fibro-blasts or embryonal cells instead of myeloma cells as partner cells. Instead of mitomycin C, other cell proliferation-limiting agents or a controlled cell irradiation can be foreseen.

A typical mitomycin-concentration is 10 ug/ml, a typical incubation time 18 hours (for 5 ug/106 cells). In this way, hybridoma cells, based on tumor-specific plasma cells, CTLs, NK-, K/ADCC-cells.and preactivated macrophages can be constructed. They can be kept in culture or frozen (PEG and/or PVP addition to DMSO); the preservation of the preactivated state by this improved cryoprotective mixture is of special relevance for repeated infusion. The use of the HAT- or HAs-medium guarantees a sufficient selection of the hybridoma cells; a time-consuming cloning is not necessary.

As next, some novel approaches in the treatment of cancer, chronic infections and autoimmune disorders, respectively, should be discussed briefly.

(1) In tumor patients and patients with(chronic) infections, especially those with (retro)viral infections, the treatment with anti-B-cell-Mabs is recommended, since the level of immunosuppressive ICs is reduced and CTL-hindering, antigen-masking specific antibodies are prevented to be synthesized. Examples of such Mabs are anti-CD19-, anti-CD20-, anti-CD21- and anti-CD22-Mab, as well as polyclonal anti-B-cell antibodies.

(2) Due to the negative impact of persistently activated macrophages on the progress of the disease, their elimination by monoclonal and polyclonal antibodies, both in tumor patients and in patients with chronic infections, including (retro)viral (HIV)ones, is recommended.

Examples: anti-CD 15-, anti-CD 14-, anti-CD1lc- and anti CD 1lb-Mates.

(3) The Mabs, described under points (1) and (2) can be injected as coctail too.

(4) The points (1), (2) and (3) are valid also for the patients with autoimmune disorders.

(5) The Mabs can be replaced by their conjugates with cytokines, radionuclids and/or cytotoxic agents to increase their efficacy.

(6) The Mabs can be also replaced by Fab/Fab')$_2$-subunits, masking—not eliminating—B cells and macrophages.

(7) An essential progress in tumor therapy, according to the invention, is the introduction of tumor cells with post-expressed MHC II, induced by interferons and/or TNFalpha. Before the reinjection, tumor cells are inactivated by mitomycin C, by heat or formaldebyde and/or glutaraldehyde.

(8) Alternatively, to point (7), hybridoma cells, arising from the fusion (in 20–40% PEG) of tumor cells with patient's MHC II-positive cells (macrophages, B cells), can be used. This cell fusion can be carried out with non-viable cells and doesn't include cell cloning.

(9) A further possibility is the presentation of tumor antigen plus autologous MHC II-antigen on the surface of liposomes.

(10) A new principle in tumor therapy is the mimicking of the strong immune reaction, observed (a) during graft rejection and (b) during the autoimmune reaction. In both cases, the immune system encounters the antigen (the allogen in organ grafts and the autoantigen in autoimmune reaction), first in its "processed" form, i.e. in context with the MHC II-complex. This favours the generation of Th and Tc cells and depresses the Ts cells being able to interact with soluble antigens directly, i.e. without antigen processing. Therefore, the in vivo situation in graft recipients and patients with autoimmune disorders should be mimicked in tumor-excised cancer patients by the injection of patient's tumor cells with the post-expressed MHC II-antigen. An additional improvement of the therapy is the use of the above-entioned constructs, consisting of the Fab/F(ab')$_2$-subunit of tumor-specific IgG or IgM, plus Fc-subunit of IgE, alone or combined with IL4.

(11) As next, the in vitro preprocessing of patient's tumor-antigen is recommended; this occurs by the phagocytosis of the soluble (e.g. 3M-KCI-extract) of tumor antigen or inactivated tumor cells, followed by the reinfusion of the involved macrophages into the patient.

(12) The procedure, based on the generation of Th-memory cells by the in vitro incubation of patient's T cells with his inactivated tumor cells, followed by the elimination of Ts cells through anti-CD8-Mabs plus complement, is of special interest. Both, the so pretreated macrophages and Th-cells mimic the situation during organ transplantation and autoimmune disorders which are characterized by a strong in vivo immune response. In this case, the in vivo immune reaction is directed against tumor cells.

(13) By the titration, i.e. "neutralization" of the soluble fraction of immunorelevant membrane structures in plasma by specific Mabs, the immunosuppressive effect of these humoral factors can be prevented. By the quantitative analysis, the patient-dependent amount of the neutralizing Mabs has to be determined in advance. Both the specific diagnostic tests and the in vivo use of the neutralizing Mab are subjects of this patent application. Examples of such molecules are the immune-response-mediating or potentiating membrane receptors in general, e.g. IL2/Tac/CD25- and T11/CD2/Leu5a/IL4-receptor, further various receptor: ligand-systems of cooperating immunocytes (integrins such as CD2: LFA3, ICAM-1: LFA1), or immunorelevant structures in general, such as CD4, CD8 and MHC II.

(14) The procedures, described under points (11) and (12) are also valid for HIV-infected persons. Classical vaccines can be essentially improved as follows: (1) by the preformation of antigen(pathogen): IgM-immunocomplexes which activates the macrophages before Ts cells are stimulated (2) by the use of preformed complexes, consisting of pathogen: IgM/IgG: complement (or C-subunit) (3) by the use of pathogen-specific IgE and/or conjugates of pathogen-specific Fab/F(ab')$_2$ subunit of IgG/IgM plus Fc-fragment of IgE (of any specificity) (4) by combining the priming with anti-CD8-Mab plus anti-B-cell-Mab and the boosting with anti-CD8-Mab alone (without anti-B-cell-Mab) (5) by masking the macrophages/monocytes with the Fab/F(ab')$_2$-subunit of the specific Mabs, after the first or during the second vaccination (6) by injecting Mabs, neutralizing gamma-interferon, TNFalpha, PGE2 and/or TGFbeta (−+IL4) 4–6-days after the first or during the second vaccination.

The next point is the prevention of tumor relapses after BMT by the potentiation of the GvL-effect, without the danger of the parallelly increased GvH-reaction. After years of research, several procedures, based on the circumvention of the critical, often fatal immunosuppressive phase immediately after the tumor removal, have been worked out. These procedures can be used per se or in combination with other techniques, described in this patent application.

One procedure comprises the admixing of donor lymphocytes, whose lifespan has been predetermined (preprogrammed) by a special 3-step-procedure, to the donor bone marrow cells. In this way, the patient gets immunocompetence, until he restores his own immune response; he is continuously able to combat infections and to prevent the reinduction of tolerance against residual tumor cells and herewith the later relapses. Before the donor T cells can provoke the GvH-disease, they die due to the preprogrammed cell death. The cell death can be predetermined by a controlled in vitro pretreatment of donor T cells with DNA-crosslinking agents. The preprogrammed cell death of immunocompetent donor T cells can be achieved also—via the intracellular irradiation—by the in vitro incorporation of radiolabeled, i.e. radionuclid/radioisotope-containing nucleosides, nucleotides, free bases and their derivatives into the DNA. Examples of such radiolabeled nucleosides are: 2'-deoxyuridine-2-$^{14}$C, further 2'-deoxyuridine-5-$^{3}$H, 2'-deoxycytidine-S-$^{3}$H and 5-bromo-2'-deoxyuridine-2-'$^{14}$C. All nucleosides and nucleotides, labeled by various redionuclides (e.g. from H,P,S and other) and added to the culture medium, are subject of this patent application.

If donoe's immunocompetent T cells are coincubated with the recipient's mitimycinC- or irradiation-inactivated MHC II (and/or MHC 1)-positive cells, the cell death-preprogramming radiolabeled nucleosides are incorporated nearly selectively into the alloreactive, recipient-recognizing donor T cells.

In the special case of the radiolabeled bromo-deoxyuridine, the prelabeled immunocompetent donor's T cells, added to the T-depleted donor-bone marrow, can be treated after the restoration of patient's own immune system ex vivo by UV-irradiation to support additionally the self-destruction of these cells by radio labeling. A similar technique of radionuclide-incorporation into the cell nucleus can be used, according to the invention, for killing of tumor cells in situ. Here, the carriers of the radioactive, tumor-destroying radiation are not tumor-specific Mabs but (a) the tumor-recognizing TIL (tumor infiltrating lymphocytes), and (b) the tumor-specific Tc/CTL(cytotoxic T cells).

A special advantage of the cellular over the molecular, i.e. Mab-mediated transport of the tumor-destroying radionuclides into the immediate neighborhood of tumor cells is the essentially intensity (density) of the cellular irradiation source. The selectivity (a) of TIL cells as carriers of radioactivity is guaranteed by the tumor-specificity of TIL-cells (Rosenberg, Anderson, Blaese), and (b)) that of tumor-specific Tc/CTL by their selective recognition of tumor antigens (TATA, TSTA, TSA). Though TIL cells belong both to the CD4-and to the CD8-positive T cells, a clear cut-off between TIL- and Tc/CTL-cells is not possible.

The preparation of TIL- and Tc/CTL-cells as carriers of tumoricidal irradiation includes radiolabeled amino acids and other radiolabeled cellular components (precursors), in addition to the radiolabeled nucleosides; they must be added to the culture medium and are incorporated into TIL- and/or Tc/CTL-cells.

A further possibility of bridging the fatal immunosuppressive phase after the removal of primary tumor or after following the BMT is the in vitro pretreatment of donor's immunocompetent cells by photosensitive dye-stuffs (e.g. psoralen), followed by their addition to the donor's T-depleted bone marrow, and their transfusion into the recipient. Later, after having protected the patient (recipient) from infections and from the clonal expansion of residual tumor cells, these photolabeled cells are selectively eliminated ex vivo by UV-irradiation. The used technique (photopheresis/PUVA) profits of predeveloped devices. For efficiency reasons, the combination of this technique with other here described techniques is recommended.

In analogous technique, photosensitive dye-stuffs are combined with or replaced by the radiolabeled or non-labeled bromo-deoxyuridine; again, the labeled cells are selectively killed ex vivo by the UV-irradiation. The use of radioactive instead of the cold isotope in BrdUr increases the efficacy of the technique. It should be combined with a preincubation of donor immunocompetent cells with inactivated MHC II (and MHC-1)-positive recipient cells which allows a selective preprogramming of cell death in the recipient-specific alloreactive subpopulation of the donor.

A further way is the in vitro transfection of donor's immunocompetent T cells with strongly immunogenic surface antigens, followed by their addition to the T cell-depleted donor bone marrow and by later transfusion into the recipient (e.g. tumor patient). The later in vivo elimination of the mature donor T cells which helps to bridge the immunoincompetent phase is carried out by antibodies, directed against the transfected membrane antigen. These antibodies can be conjugated with cytotoxins in order to increase their efficacy. A further modification of this technique is based on the addition of T cells of a second MHC-incompatible donor to the T depleted bone marrow of the first donor. After the restoration of patient's own immunocompetence, mature histoincompatible donor T cells are eliminated in vivo by allotypic antibodies or corresponding immunotoxins. All these techniques can be used alone or in different combinations. The next procedure is based on the cumulative (additive) effect of DNA-damaging by cytotoxic agents and/or irradiation. The immunocompetent cells of the donor are treated first in vitro by the sub-lethal dose of the DNA damaging cytotoxic agent and/or irradiation and later in vivo after the finished mission (bridging of the fatal immunosuppressive interphase, before the restoration of patient's immune competence) by a second (lethal) dose of cytotoxic agent(s) or irradiation. The strong GvL-effect of the so pretreated donor bone marrow can be further intensified if the donor's immunocompetent T cells to be admixed to the donor bone marrow are predepleted of alloreactive subclones and activated in a tumor-specific or non-specific way, before they have been injected into the patient. In addition, the technique, based on a novel type of immunocompetent T cells which is characterized by a "frozen" activated functional state, should be described briefly. Details about this novel cell type, implicating a constitutively activated state without cell proliferation, follow below.

Cells of this novel type can be added to T-depleted donor bone marrow and must not be later on eliminated in vivo, because their ability to proliferate is genetically switched off. Characteristically for all these techniques is (a) a strongly increased GvL-effect, without a simultaneous GvH-reaction, (b) opening of new ways for histoincompatible BMT, (c) the option of an additional tumor-specific and/or non-specific preactivation of immunocompetent T cells, admixed to the T-depleted donor bone marrow, and (d) the impact on both the GvH- and HvG-reaction which minimizes the BMT-associated complications.

These facts support the inventor's idea to introduce BMT obligately in the patients with solid tumors. According to the invention, the classical BMT could be replaced by the simple exchange of patient's (recipient's) T cells by T lymphocytes of the donor in patients with solid tumors. This can be carried out by an in vivo depletion of patient's T cells by specific Mabs or immunotoxins and transfusion of healthy donor T cells; the histoincompatibility problems can be overcome by the above described special pretreatment of immunocompetent T cells.

According to a further therapeutic model, the bridging of the fatal immunosuppressive phase, following the tumor excision or BMT can be achieved by autologous or allogeneic LAK-cells plus rIL-2. Since LAK-cells consist of ca. 90% NK-cells and of ca. 10% non-MHC-restricted CD3+-T cells, the in vitro predepletion of CD3+, cells is recommended in the case of allogeneic LAK-cells. Alternatively, the complete LAK-population can be treated by one of the above described cell death-preprogramming procedures. The so pretreated allogeneic LAK cells are added to the donor bone marrow before their injection into the recipient. An important positive "side effect" is the in vivo killing of recipient's HvG-inducing residual T cells. In this way, the complications of a radical recipient conditioning could be prevented. This HvGR-inhibiting effect is based on the property of NK- and LAK-cells to recognize and to inactivate—via the 4F2/TNKTar-antigen—fastly proliferating cells. The plasmapheresis brings some additional advantages in the autologous or allogeneic EMT. The removal of immunosuppressive factors, belonging primarily to the immune complexes, to the solubilized cytokine- and growth factor-receptors, as well as to the prostaglandins, has been neglected in conventional BMT. A further improvement is the addition of fibroblast to the donor BM. The situation following BMT shows a common element with the situation of immunocytes in the limiting dilution-test, in which the added fibroblasts, by secretion of growth factors, make the growth and the survival of immunocompetent cells possible.

Though there are trends to shorten the phase of immunoincompetence in tumor patients and BM-recipients by cytokines (G-CSF, GM-CSF), fibroblasts, admixed to the donor bone marrow are expected to secrete a much broader spectrum of cytokines.

As next, the addition of donor-macrophages to donor-BM is recommended; in this way, the cooperation of accessory cells (APC) with T cells in the critical post-transplantation phase is guaranteed. The temporary masking of recipient-macrophages (to inhibit the preexistent suppressor monocytes) is also of interest.

The next point is the selective in vivo depletion of the recipient macrophages/monocytes (e.g. by specific Mabs or immunotoxins) and/or the addition of donor-macrophages to donor bone marrow. Finally, the use of neutralizing Mabs, directed against all those cytokines which allow the mutual activation of macrophages, T4 cells and NK cells in the critical phase of the GvH- and HvG-reaction, is recommended. So, the clonal expansion of alloreactive subpopulations, following allogeneic bone marrow and organ transplantation, can be prevented by neutralization of TNF alpha, IL-1, IL-6 and/or gamma IFN. As next, a novel cell type should be described which is characterized by the "frozen", i.e. constitutively activated functional state and by a parallel switching off of the cell proliferation. This state is associated with the cell arrest in the $G_1$- or $G_2$-phase and with a permanently increased level of the intracellular $Ca^{2+}(Ca_1)$. In the case of ex vivo generated LAK- and TIL-cells, the problem of a rapid activity drop of these cells in vivo could be solved by the corresponding cell modification. This in vivo inactivation of LAK- and TIL-cells stems from the induction of lipocortin/lipomodulin by plasma corticosteriods (cortisol) and can be prevented in two ways: (1) by the constitutive, proliferation-free activation of LAK- and TIL-cells, and (2) by the transfection of LAK- and TIL-cells with the CDNA, encoding the cortisol-cleaving enzymes, such as 20alpha-hydroxysteroid-dehydrogenase and B-glucuronidase.

The T cell-activation (a) by different cytokines, such as IL-2, IL-3 and CSF-1/M-CSF, and (b) by (processed) antigen occurs in the same way, i.e. via the activation of the PI (phosphoinositol)-dependent PLC (phospholipasec) and results in the increase of the intracellular $Ca^{2+}$-level.

The constitutively increased $Ca^{2+}$-level in the cell cycle-arrested cells (subject of this patent application) opens a novel way of cell activation. A special advantage is the cell activation and the maintaining of this activated state even in the absence of the specific signal, e.g. the processed antigen in the case of helper T cells. In other terms, the constitutively $increased\ Ca_{i2+}$-level in the cell cycle-arrested cells confers to these cells the genetically predetermined (highly specialized) function, e.g. the production of specific antibodies or the CTL- or ADCC-activity. A further advantage is the inner stability, i.e. the resistance against the specific or non-specific suppression by suppressor factors, such as prostaglandins (e.g. PGE1/E2) or corticosteroids, without the danger of an uncontrolled cell proliferation (because of the cell cycle-arrest).

This goal can be reached in two ways: (a) by hybridization of cells with the desired function, e.g. plasma cells, CTL/Tc, T4/Th etc. with immortalized cells (autologous tumor cells of the patient or transformed cells of other origin), followed by the treatment of formed hybridoma cells by cell death-preprogramming techniques, as described above, and (b) by a double transfection of the cells, showing the desired function (B, T4, T8), with the sense-cDNA, encoding the constitutive cell activation plus antisense-cDNA, encoding the switching off of cell proliferation.

Ad (a): The cell death-preprogramming treatment can occur either in hybridoma cells or in immortalized partner cells, before these have fused to give hybridoma cells.

The rejection of hybridoma cells, based on non-allogeneic immortalized cells, must be prevented (a) by their repeated incubation in the presence of the alloantigen-specific antibody, or (b) by transfection of the cells with the histospecific antisense-cDNA.

Candidates for the immortalized partner cells are those transformed cells which maintain an increased intracellular $Ca_i^{2+}$-level by autocrine or paracrine mechanisms or such transformed cells which are able to maintain—independently of external signals—the activated state either by the constitutive, ligand-dependent activity of tyrosine- or serine/threonine-kinases or by the continuing PI-conversion to PIP2.

Ad (b): The double transfection of the target cells, showing the desired function (B,T4,T8 . . . ) (b1) with sense-cDNA, encoding the constitutive expression of cell-activating signals, plus (b2) with antisense-cDNA, encoding the turning off of cell proliferation, creates a permanently "turned on", non-proliferating cell which doesn't need any specific signals (e.g. processed antigen) for its activation.

These novel cell constructs have an enormous practical relevance. Examples are (1) the intracranial injection of NGF (nerve-growth-factor)- and/or DOPA-secreting, long-lasting, fibroblast-based cells constructs which cannot be down-regulated by plasma suppressor factors and are of special interest in the treatment of M. Alzheimer and M. Parkinson, further (2) the cytokines and growth factors-producing cell constructs which support patient's immune system, following high-dose (radio)chemotherapy and BMT, as well as (3) cell constructs, based on tumor-specific plasma cells which are able to produce anti-tumor-Mabs in situ, preventing in this way the induction of neutralizing immunoglobulins.

As the sense-cDNA, encoding cell activating signals (1) the cDNA, encoding various cytokines or (hematologic) growth factors and/or their receptors, further (2) the PLC- and PLA2-encoding cDNA, (3) the cDNA, encoding different cytoplasmic serine/threonine-kinases, and (4) the cDNA, encoding various protein-kinases, such as C-kinase, Ca/calmodulin-kinase, casein-kinase II and G-kinase, are recommended.

The prevention of cell proliferation can be achieved by the antisense-cDNA of all cell division-inducing factors. Examples are (a) cyclinA, cyclinB 1, c-ras, c-raf, PSTAIRE, MPF, $p34^{cdc2}$, p13, further (b) the DNA-transcription factors like AP-1 (AP-I) and AP-2(AP-II), and (c) DNA-polymerase-alpha, PCNA and (protein)elongation factor (elF-2/elF-2p). PSTAIRE is a cdc2-subregion (aminoacids 42–56) and belongs, like $p_{34}^{cdc2}$, to the family of cell cycle-specific protein-kineses. The PCNA (proliferating cell nuclear antigen)is a 36kD-intra-nuclear-polypeptide and component of polymerase-delta; the MPF stands for mitose- or M-phase-promoting-factor.

Alternatively to these antisense-cDNAs, various sense-cDNAs, encoding suppressor-oncogenes, such as plO5RB and p53 can be transfected to prevent uncontrolled cell proliferation. By transfection of extra-copies of the p53 and/or RB-cDNAs,somatic cells, including leukocytes, can be made more resistant against different carcerogenic agents.

The uncontrolled proliferation can be switched off also by cell fusion with normal cells, expressing the wild type or the wild-type p53.

One of the points, according to the invention, is the prevented expression of the MHC II or MHC I complex on the cell construct, achieved by the transfection of the MHC II or MHC I-encoding antisense-cDNA. The antisense-cDNA can be replaced (a) by ribozymes, (b) by psoralent derivatives of the antisense-oligonucleosides or -oligonucleosidemethylphosphonates, and (c) by antigen- and antisense-oligonucleotid-intercalator-conjugates.

(a) The advantage of ribozymes, called also "catalytic RNA", over the corresponding antisense-cDNA is their irreversibility as they cleave the sense-DNA. The smallest and simplest self-cleaving domain of ribosome is the "hammerhead"-structure, e.g. the "structure I", described by Uhlenbeck or the "form IV", reported by Haselhoff and Gerlach.

(b) The psoralene-derivatives of antisense-oligonucleosidmethylphosphonates are also irreversible in their action; here, the desired sense-DNA is switched off by the photoinduced DNA-crosslinking.

(c) When the technique, based on oligonucleotid-intercalator-conjugates is used, the irreversibility is achieved by the conjugation of antisense-cDNA or -RNA with the chemically ($Cu^{2+}$-phenanthroline) or photochemically (ellipticin) inducible intercalator-molecules.

The immunotherapy of malignancies and autoimmune disorders, as well as of bacterial and (retro)viral infections is based on the same principles as the improvement of conventional vaccines and prevention of graft rejection, namely (a) on the deblockade of the hyperactivated state of immunocompetent cells and/or (b) on the elimination or inactivation of hyperactivated effector cells ("microimmunosurgery"). (a) This deblockade of the hyper-activated state of immunocytes can be achieved, according to the invention, by combining agents which block the "voltage-operated" and/or "receptor-operated" $Ca^{2+}$-channels ("component I"), with agents which reduce the intracellular cAMP or the. cAMP/cGMP-ratio, respectively ("component II").

The "component I" comprises "classical" Ca-antagonists (Ca-channel-blockers) of all subtypes, e.g. phenylalkylamines, dihydropyridines, benzothiazepines, piperazines, quinoxalines, quinazolines (e.g. bepridil and perhexilin). Alternatively or additionally, a parallel inhibition (blockade) of alpha- plus B adrenoceptors, of H2-plus H1-histamine receptors, of A2- plus A1-adenosine receptors, of 5-HT/serotonine) receptors and/or receptors of various inflammation mediators (e.g. bradykinin, kinin-cascade, complement-cascade, especially c5a, c4a, c3a, PAF etc.) is recommended. Examples of preferred combinations are listed below; they can be combined with sub-dosed nitro-compounds, including molsidomine, Ca-overload.blockers, e.g. cinnarizine, Ca-antagonists, BRM and/or cytokines. The combination of molsidomine and nicergoline (an alpha-blocker), with or without Ca-overload-blocker(s) (e.g.cinnarizine) is of a special interest.

The "component II", comprises cAMP/cGMP- or cAMP-reducing agents. Examples are antagonists of all cell receptors which are coupled via the Gs-protein to the membrane-associated adenylate cyclase (AC). This effect is increased if agonists of $G_p$-, $G_i$- or $G_o$-protein-coupled receptors and/or of cGMP-increasing, $Ca_i$, reducing nitro-compounds (e.g. isosorbid-mono- and -dinitrate, glycerol-trinitrate/nitroglycerol, erythrit-tetranitrate, pentaerathrit-tetranitrate, amylnitrite, molsidomine) are given parallelly. The antagonists of those Gs-coupled receptors whose normal, physiological agonists bind at the same time $P_p$-,$G_i$- or $G_o$-coupled receptors are of a special interest. After having blocked the. Gs-coupled receptors, the Gs-coupled receptors, the endogenous ligand bind the $G_p$-, $G_i$- or $G_o$-coupled receptors to a higher degree. In this way, B-blocker achieve 2 effects, the cAMP-drop and the cGMP-rise in cytosol of immunocompetent target cells. Examples of such endogenous agonists are catecholamines (adrenaline and nonadrenaline), histamine and adenosine. So, the antagonists of B-adrenoceptor (on immunocytes, e.g. T cells and monocytes/macrophages) cause catecholamines, primarily adrenaline, to interact with the alpha- instead of B-adrenoceptor. Similarly, the antagonists of H2-histamine receptor make the histamine ligate the cAMP-lowering H1- instead of the cAMP-increasing H2-receptor. In the presence of A2-antagonists, the endogenous agonist adenosine binds to the cAMP-depressing A1- instead of to the cAMP-raising A2-subtype Pl-adenosine receptor.

It is also advantageous to use the agents which inhibit reversibly both, the Ca- and the Na-channels. The working mechanism is the increase of the resting potential of immunocompetent cells which is decreased during the hyperactivated state. This class of substances comprises (a) some Ca-antagonists like cinnarizine, flunarizine, fendiline, bepridil, tiapamil and partly verapamil and gallopamil, further (b)sub-dosed antiarrhytmics (class I to IV), especially the combination of class ID with class III, due to the equilibrated K-efflux (class IB) and K-influx (class III) and synergism in the inhibition of Na-channel (among these agents are adrenoceptor-blockers sotalol and propranolol). The combination of cinnarizine and propranolol is of a special interest.

The central point of this invention is the combination of agents which decrease the cAMP-level or the cAMP/cGMP-ratio with those which block the "voltage-operated" and/or "receptor-operated" Ca-channels. In special cases, the "component I" and "component II" are identic. So, some special nitro-compounds, such as syndnonimine derivatives (e.g. mosidomine), show both effects (cGMP-rise, $Ca_i$-decrease); they are also subject of this invention.

Both, the therapy of the diseases discussed above and the efficiency of conventional vaccines can be further improved by methylxanthines, by pHi-increasing substances, ba redox-potential, GSH/GSSG and NADP)H/NAD(P)$^+$ correcting agents, as well as by ionic homeostasis and K-balance influencing substances.

(b) Inactivation/elimination of hyper- or persistently activated immunocompetent cells.

The principle of this in vivo inactivation or depletion of hyperactivated effector cells is the "microimmunosurgery", a new technique which would compete with or complement the gene-therapy in future. The principle is the selective inactivation of disease-inducing and disease-maintaining lymphocyte-subclones by the combination of (b1) panT- or T subclass-specific Mabs or Mab-derived immunotoxins, plus (b2) alloreactive T cells of a healthy donor. This combination of humoral (Mab) and cellular (allogeneic T cells) technique is able to increase essentially the efficiency of the Mab-mediated depletion of pathogenic immunocyte-subclones, as shown in animal model. Tumor patients as well as patients with (chronic) infections (including HIV) and those, suffering from CFS (chronic fatigue syndrome) show a strongly increased number of CD8-positive (Ts) and/or HLA-DR(MHC II)-positive T cells. By the combination of anti-CD3- or anti-CD8-Mabs plus allogeneic donor-PBM/PBL or donor T cells whose cell death is "preprogrammed"/"predetermined" by a special in vitro treatment, the meotioned pathologic (hyperactivated) CD8:HLA-DR-positive effector cells can be selectively eliminated in vivo. In this way, a 94–100%-survival rate in tumor-bearing mice could be achieved.

The "preprogramming" of cell death in allogeneic donor PBM/PBL or T cells is a multistep in vitro procedure, comprising the following steps:
(1) Synchronization of "donor effector cells" (a) by their incubation in serum-free medium, followed by the incubation in serum-containing medium, or (b) by cell incubation first in the absence and later in the presence of essential aminoacids (e.g. isoleucin), or (c) by cell incubation in the presence of synchronizing cytotoxic agents, such as vinchristine, hydroxyurea or bleomycin.
(2) Treatment of "donor-effector cells" by (a) bifunctional alkylating agents, i.e. DNA-cross-linking agents (e.g. mitomycin C) and/or (b) by inhibitors of the enzyme ribonucletoid-reductase (e.g. hydroxyurera) which block the DNA- but not the RNA- or protein-synthesis.
(3) Incubation of "donor effector cells" in the presence of inhibitors of DNA-reparases (DNA repair system) (e.g. hydroxyurea).
(4) A thorough washing of cells, e.g. by PBS or RPMI 1640.
(5) Infusion of so pretreated "donor effector cells" into the recipient (e.g. tumor patient).

An alternative procedure consists of the incubation of "donor effector cells" (a) with radiolabeled DNA-constituents (purine- and pyrimidine bases) and/or (b) with radiolabeled aminoacids.

A further alternative is the irradiation of "donor effector cells", followed by their incubation in the presence of inhibitors of DNA-reparases (e.g.hydroxyurea).

In the special case of autoimmune disorders, the target cells of "preprogrammed" alloreactive donor T cells are also the HLA-DR(MHC II)-positive autoaggressive T cells (mostly T4, partly T8 cells).

The procedure consists of the in vivo depletion of T cells (by anti-panT/CD3-Mabs) or their T8 and/or T4 subclass. Because of the high costs for the "pure" Mabs and Mab-derived immunotoxins, their combination with cytotoxic agents, especially cyclophosphamide is recommended.

A further improvement of the technique is the reinfusion of patient's peripheral blood cells which have been preactivated ex vivo against the donor PBMs/PBLs, into the patient, after the premanipulated donor effector cells have eliminated the pathologically activated recipient lymphocytes.

As animal experiments have shown, the efficiency of "microimmunosurgery" is so high that the donor effector cells are able to lyse patient's pathologic leukocyte-subclones even (a) without a preceding in vivo Ts-depletion (by Ts- and/or panT/CD3-specific Mabs), though the combined attack on the cellular and humoral level remains the most efficient approach. All experiments, however, show an enormous rise in their efficacy when the in vivo used Mabs are combined with the cell death-preprogrammed effector cells. This concerns the therapeutically used anti-tumor-Mabs, the Mabs, utilized in the recipients of organ grafts (e.g. anti-CD3-Mabs) and the Mabs, used in the treatment of autoimmune disorders (e.g. anti-CD4-Mabs).

A further possibility (a) to bridge the critical immunoincompetent phase, e.g. after the excision of primary tumor or following the BMT, and (b) to prevent GvHR (but not GvLR), is as follows:

(a) Patients, e.g. those with solid tumors, are first "conditioned" by anti-CD3-Mab (or the corresponding immunotoxin), or by the Mab-saving combination of cytotoxic agent (e.g. cyclophosphamide=plus Mab.

b) In addition, the CD8:HLA-DR/DQ-double positive suppressor fraction is eliminated by means of "microimmunosurgery".

(c) The next step is the in vivo depletion of donor effector cells by patient's (i.e. autologous) T cells or PBMs/PBLs. The ratio between the autologous T cells or PBMs/PBLs (point (c)) on the one hand and the corresponding leukocyte-subpopulations of the healthy donor (point (b)) on the other hand should be 3:1 to 10:1; in this case, the cell death-programming can be omitted. Both, the donor effector cells (point(b)) and the autologous effector cells (point (c)) can, but must not be prealloactivated. It is advantageous if parental PBMs/PBLs are used as donor effector cells.

The presensibilization of donor alloreactive effector cells against the recipient lymphocytes brings an additional advantage: The so presensibilized (primed) donor effector cells are blastogenically pretransformed and can be activated in vivo, in some analogy to the effector cells of the secondary MLC and those of the PLT 1–2 days earlier as the non-primed clones. This fact confers to the presensibilized (primed) donor cells the crucial advantage, that they are able to eliminate—following their infusion into the patient—his pathologically (hyper)activated, MHC II-positive subpopulations before the patient's defense against these therapeutically utilized donor-effectors can be organized. For this reason, the number of donor effectors to be transfused can be reduced and the cell death-preprogramming possibly omitted.

(c) Improvement of organ grafts (kidney-, heart/lung-, liver-allografts)—The acute rejection, leading to the loss of the graft organ can be essentially improved, according to the invention, if the classical procedures, based (a) on a generalized immunosuppression (azathioprine, prednison, (methyl)prednisolon, cyclosporinA), and/or (b) on the in vivo T cell depletion by anti-CD3-Mabs or ALG or ATG, are completed or partly replaced by the "microimmunosurgery" or by the cell death-preprogrammed effector cells.

(d) Improvement of conventional vaccines—The same principle (deblockade and/or inactivation/elimination of hyperactivated effector cells) can be used to improve the conventional antibacterial and anti(retro)viral vaccines, including the anti-HIV-vaccines; the target cells are here the CD8: MHC II-double positive suppressor effector cells. The principle is the increase of the absolute number of blastogenically pretransformed, pathogen-specific Th-, Tc/CTL- and/or B(plasma) cells by (a) deblockade and/or (b) inactivation/elimination of pathogen-specific Ts cells. In an early phase, these Ts inhibit the generation of pathogen-specific Th-, Tc/CTL- and B-memory cells. By (a) deblocking and/or (b) inactivating/eliminating the Ts-cells, the clonal expansion of "positive" memory cells (Th, Tc, B) is strongly increased and the protection of infection significantly improved.

(a) The deblocking of Ts-cells occurs by the combination of "component I" and "component II".

(b) The inactivation/elimination of CD8:HLA-DR/DQ-positive Ts-cells is performed by alloreactive, cell-death-preprogrammed effector cells (see above).

(c) The "immunologic memory", induced in a pathogen-specific way by vaccination, can be further improved by eliminating in vivo the pathogen-specific Ts-cells of the vaccinated person with subset (CD8/Ts)- and/or panT (CD3)-specific Mabs or corresponding immunotoxins (d) The number of pathogen-specific Th-, Tc- and B-cells can be increased also by delaying the antibody-production through Mabs (and immunotoxins), directed against (d1) B-cells, (d2) Th(T4)-cells, (d3) B-plus Th(T4)-cells, (d4) monocytes/macrophages ("suppressor monocytes"), and/or (d5) B-cells plus suppressor-monocytes.

Again, "pure" Mabs can be replaced by the Mabs-saving mixture of cytotoxic agents (e.g. cyclophosphamide) plus Mab.

(e) support and partial replacement of glucocorticoids (e.g. cortison) by low-dosed antagonists of Gi(Gp,Go)-coupled receptors and/or by low-dosed agonists of Gs-coupled receptors.

Glucocortocoids, characterized by strong side-effects, can be supported or partly replaced by sub-dosed blockers of Gi-, Gp- or Go-coupled receptors and/or by low-dosed ligands of Gs-coupled receptors. These agents can be combined with sub-dosed Ca-antagonists.

The indication of these novel combination preparations corresponds to that of "classical" glucocorticoids. Again, the antagonists of those Gi(GP, Go)-coupled receptors which share the endogenous ligand with a Gs-coupled receptor (e.g. catecholamines, histamine, adenosine) are of a special interest. With such combinations, other clinically used immunosuppressive agents (e.g. cyclosporine, FK506, rapamycin, azathioprin, cyclophosphamide) can be supported or partly replaced.

Since the hyperactivated state of effector cells (T cells, macrophages etc.) is an important element in the pathogenesis (a) of cancer (b) of autoimmune disorders (c) atherosclerosis (d) infectious diseases (including HIV), the procedures, described under the point (a) ("Deblocking of hyper- or persistently activated immunocompetent cells") and under the point (b) ("Inactivation/elimination of hyper- or persistently activated immunocompetent cells") are valid for all these diseases.

The reduction of background-signals, i.e. "filtering out" of non-specific (non-productive) transmembranal signals increases the susceptibility of immunocompetent cells for specific, immunorelevant signals.

1 Combination of sub-dosed B-(B1- plus b B2-) and sub-dosed alpha-(alpha1- plus alpha2) adrenoceptor blockers (antagonists) (objective: prevention of hypoergic or anergic state of hyperactivated immunocompetent cells by lowering the level of non-specific background-signals).

1.1 Combination of preparations on pindolol-basis (e.g. durapindol/–15/–retard (26.039) or pinbetol/forte (26.067) plus preparations on phenoxybenzamine-basis (e.g. dibenzyran 1/5/10(81.091)). Pindolol is a B1- plus B2-sympatholytic, phenoxybenzamin an alpha1- plus alpha2-blocker. Recommended dose: 1×15 mg/d or 3×5 mg/d or 2–3×1 mg/d dibenzyran.

2 Combination of sub-dosed B-(B1- plus B2-)-adrenoceptor-blockers with sub-dosed alpha1-receptor-antagonists, blocking at the same time the H1-histamine and the 5-HT(serotonin) receptor (objective: see point (1)).

2.1 Combination of drugs on pindolol-basis (e.g. durapindol/–15/–retard (26.039), or pinbetol/forte (26.067)

plus preparations on indoramin-basis (e.g. wydora/50 (16.039)). Indoramin is the antagonist of alpha1-adrenoceptor, of H1-histamine receptor and of 5-HT receptor. Recommended dose: durapindol (see above); indoramin 1×25 mg/d.

Combination of sub-dosed B- (B1- plus B2-) adrenoceptor-antagonists with sub-dosed alpha- (alpha1- or alpha2-) receptor blockers (objective: see point (1) and (2)). 3 Combination pf preparations, based on 3.1.1. alprenolol (e.g. aptin (26.002)), 3.1.2. bupranolol (e.g. betadrenol 50/–100(26.017)), 3.1.3. penbutolol-sulfate (e.g. betapressin (26.019)), 3.1.4. bisoprololfumarat (e.g. concor 5/10 (26.025)) or 3.1.5. carteolol (e.g. endak 5/10 (26.046)) plus preparations, based on 3.1.1. urapidil (e.g. ebrantil 30/60/90 (16.032)), 3.1.2. doxazosinmesilate (e.g. cardular 1 mg/–2 mg/–4 mg (16.029) or diblocin 1 mg/–2 mg/–4 mg (16.030)) or 3.1.3. terazosin (e.g. heitrin 1/2/5 (16.035)). Recommended doses: aptin-duriles 1×200 mg/d; betadrenol 1–2× 50 mg/d; betapresin 0, 5–1×40 mg/d; concor 1×5 mg or 1×10 mg/d; endok 5 mg/d; ebrantil 30 mg/d, cardular 1 mg/d; diblocin 1 mg/d; heitrin 0,5–1 mg/d.

4 Combination of sub-dosed H2- and H1-histamine receptor antagonists (objective: see above).

4.1 Combination of preparations, based on cymetidine (e.g. sigacimet 200/–400/–800 (59.102) or tagamet 200/–400/–800 (59.105) or H2-blocker ratiopharm (59.096) plus preparations, based on 4.1.1. oxatomid (e.g. barpet (07004)), 4.1.2. bromopheniramine-hydrogenmaleate (e.g. dimegan (07.005)), 4.1.3. dimetindenmaleate (e.g. fenistil (07.006)) or 4.1.4.terfenadine (e.g. hisfedin (07.009)). Recommended doses: sigacimet 1×200 mg/d; tagamet 1×200 mg/d; H2-blocker ratiopharm 1×200 mg/d; barpet 1×30 mg/d; dimegan 1×12 mg/d; fenistil 1×1 mg/d; hisfedin 0,5–1×60 mg/d.

5 Combination of sub-dosed antagonists of A2- plus A1-P1-purinergic (adenosine) receptors (objective: see above. 5.1 Combination of preparations, based on methylxanthines (theophylline) (e.g. aerobin mite (27.102) or contiphyllin retard (27.113) or euphyllin N (27.125)) plus preparations, based on ipratropium-bromide (e.g. atrovent (27.048) or itrop (09.028)). Recommended doses: aerobin 0,5–1×200 mg/d; contiphyllin 0,5–1×300 mg/d; euphyllin N 1×73 mg/d; atrovent 0,5–1×200 mg/d; itrop 0,5–1×10 mg/d. Combinations, based on cromoglicinic acid (diNa-salt) and ketotifen-hydrofunarate are also of an interest.

Sub-dosed antagonists under the points (1) (2) (3) and (4) can be combined. In this case, the dose has to be reduced to 5–50% of the dose, quoted under the points (1) (2) (3) and (4). The strongly sub-dosed antagonist under the points (1) (2) (3) and (4) can be combined with conventional Ca-antagonists and/or with sub-dosed agonists of Gp- and Gi-coupled receptors.

(I) Malignancies (1) The restoration of the immunocompetence following the sublethal irradiation or high-dose chemotherapy can be accelerated—according to the invention—if cytokines such as M-CSF or GM-CSF are combined with (a) antagonists of Gs-coupled receptors, (b) agonists of Gi(Gp/Go)-coupled receptors, and/or (c) Ca-antagonists.

(2) Therapeutic approaches, based on tumor-specific Mabs (and corresponding immunotoxins), can be improved essentially by combining these Mabs (a) with anti-CD3- and/or anti-CD8-Mabs, and (b) with "micro-immunosurgery", tumor patients are (a) first treated by the combination of Mab-saving cyclophosphamide plus anti-CD3- or anti-CD8-Mab, then (b) injected by alloreactive donor effector cells (PBM/PBL or T cells) which can be primed against the recipient and (c) treated again by cyclophosphamide plus anti-CD3- or anti-CD8-Mabs in order to eliminate the alloreactive donor cells, and (d) finally reinjected with the autologous PBM or T cells, collected before the start of therapy, to restore the recipient's immunocompetence. In a simplified version, the step (c) can be omitted.

(4) The reinduction of tumor-specific Ts cells can be prevented (a) by Mabs, directed against immature T cells (e.g. anti-T6-, antiT9-, anti-TlO-Mabs), (b) by antagonists of Gs-coupled receptors, and/or (c) by agonists of Gi-coupled receptors.

(5) To prevent an early RES-elimination of allogeneic effector cells during the "microimmunosurgery", a simultaneous injection of allogeneic erythrocytes or inactivated autologous erythrocytes is recommended (temporary "RES-blockade").

(6) The combination of (a) insuline or antidiabetes with (b) glucose or di- and tricarbonic acids can amplify the above described deblocking process of hyperactivated macrophages and T cells. Instead of di- and tricarbonic acids, their alkali-salts are recommended, which lead to the rise of intracellular pHi:

(7) The combination of (a) amiloride plus plasma-acidifying agents (e.g. $NH_4Cl$, Iysine.HCl, methionine HCl) with (b) TNF (or TNF-inducers such as LPS) or interferon, augments their ROI-mediated target cell damaging by inhibiting the synthesis of ROI-cleaving enzymes (e.g. SOD).

(8) Since hyper- or persistently activated effector cells (macrophages, T cells etc.) represent a common element (a) in neiplastic, (b) in autoimmune diseases (c) in atherosclerosis, (d) in bacterial and (retro)viral infections, including HIV, and (e) in vaccines, the use of antagonists of Gs-coupled receptors and of agonists of Gi(Gp)-coupled receptors, as well as of Ca-antagonists/Ca-overload-blockers is recommended in all these situations.

(9) The efficiency of "microimmunosurgery" can be further increased by the in vivo or in vitro sensibilization of donor effector cells against the recipient (patient). Blastogenic pretransformation confers the donor effector cells a higher efficacy and a time advantage of 24 days which allows these donor cells to inactivate the patient's pathological subdlone(s) before the recipient can organize the anti-donor defense. In this way, the pretreatment of the recipient (patient) by cyclophosphamide plus Mab can be reduced to a minimnum.

(10) Agents, increasing the intracellular cGMP, such as (a) nitrocompounds (e.g. glycerolnitrates, isosorbit-mono- and dinitrates), vasodilators (e.g. minoxidil, (di)hydralazine, Na-nitroprusside) and (c) molsidomine can be used alone or in combination with BRMs, lymphokines, growth factors, methylxanthines (e.g. theophylline), Ca-antagonists or Ca-overload-blockers, agonists of Gi(Gp)-coupled receptors, antagonists of Gs-coupled receptors and/or pHi-increasing or redox potential-correcting substances.

(11) Since vasodilators (e.g. nitrocompounds) and molsidomine inhibit the IP3-mediated $Ca^{2+}$-mobilization, they can be used, alone or combined with Ca-antagonists, for a rapid deblockade of those hyperactivated effector cells which show a strongly increased $Ca^{2+}$-level due to an excess of signals, as observed e.g. in chronic inflammation and autoimmune disorders. Favorable is the combination with pHi-increasing and/or redox potential correcting agents.

(12) The combination of molsidomine plus nicergoline (with or without cinnarizine) is of a special interest.

(13) Infection and inflammations can be treated by combining NSAID with sub-dosed (a) antagonists of Gs-coupled receptors (b) agonists of Gi(Gp)-coupled receptors and/or (c) sub-dosed Ca-antagonists (optimally: Ca- and Na-channels-inhibiting Ca-overload-blockers, such as cinnarizine).

(14) With the same classes of substances, the in vitro generation of LAK- and TL-cells could be improved essentially.

(15) The suppressor-monocytes seem to play a crucial negative role in the process of immunosuppression. Therefore, they have to be depleted in vivo by anti-Macrophage-Mabs (or immunotoxins), along with the neutralization of their secretory products (monokins) by Mabs, directed against TNFalpha and IL-1. In addition, the macrophage-stimulating gamma-IFN must be neutralized by the specific Mab.

The effector cells, active in the "microimmunosurgery" process, seem to inactivate both the hyperactivated T cells and the pathologically activated macrophages.

(16) The cGMP-synthesizing guanylate cyclase (G.C.) can be stimulated, according to the invention, (a) by nitro compounds ("organic nitrates"), such as glycerol-, erythrite- and isosorbite-nitrate, (b) by further vasodilators, such as minoxidil, (di)hydralazine, Na-nitroprusside, (c) by compounds such as arginine, N-methyl-D-aspartate(NMDA), L-glutamate, S-acetylthiocholin-iodide, paraquate, D- and L-ornithine, further extreme low concentrations of NO and CO. The most act via stimulation of NO-synthetase (NOS). The monokines such as TNFalpha and L-1 and lymphokines, such as IFN-gamma (a) switch the cell function from the cell proliferation to the cell differentiation, and (b) induce the secretion of numerous cytokines via the $H_2O_2$-intermediate. Interestingly, the $H_2O_2$ per se is able to induce, at very low concentrations, the TNF-production. The NO-synthesis goes parallel with the ROI ($H_2O_2$)-formation and is dependent in its last step (oxydation of the hydroxylamine-intermediate) on the cooperation with the compound I (catalase: $H_2O_2$-complex). The NO is oxydized to $NO_2$ and $NO_3$.

The cGMP-synthesis and mediately the secretion of cytokines can be achieved also by extremely low concentrations of ROI (e.g. $H_2O_2$ or Mg-peroxide or $(NH_4)_2S_2O_4$).

On the other hand, by the inhibition of NO-synthetase or by ROI-scavengers and reducing agents (e.g. N-acetyl-cysteine, glutathione, cysteine, ascorbate, penicillamine etc.), the (hyper)production of cytokines can be inhibited.

(17) The efficacy of the treatment can be increased by the intratumoral/intralesional application (a) of NOS-activators (b) of agonists of Gi(Gp)-coupled receptors and/or (c) of antagonists of Gs-coupled receptors.

(18) Since the cGMP-increasing agents (e.g. nitrocompounds, molsidomine) decrease the $Ca_i$-concentration, the combination of these compounds with $Ca_i$- and pHi-increasing agents is recommended. By a fine mutual balancing of these substance classes, first the energy of immunocompetent cells, caused by hyperactivity, can be broken by nitrocompounds and subsequently the biosynthesis of cytokines and growth factors can be induced by a parallel $Ca_i$- and pHi-elevation.

(19) On the other hand, the combination (a) of $Ca_i$-reducing stimulators of NOS (b) with agonists of Gs-coupled receptors or with antagonists of Gi(Gp)-coupled receptors and/or (c) with Ca-antagonists results in the inactivation of pathologically hyperactivated subclones. This effect can be strengthened by the TNF (or TNF-inducers, like LPS), IFN-gamma and IL-I.

Of a special interest is also the combination of Ca-overload-blockers, e.g. piperazines (cinnarizine, lidoflazine, flunarizine) with Ca-antagonists (controlled $Ca_i$- and cGMP-rise).

(20) The use (a) of agonists of Gi(Gp)-coupled receptors, (b) of antagonists of Gs-coupled receptors, and/or (c) of NOS-stimulating compounds helps to save cytokines and growth factors. By a fine mutual balancing, a parallel $Ca_i$-, pHi- and cGMP-rise and herewith a maximal cytokine production can be achieved.

(21) The pretreatment ("conditioning") of recipient, i.e. tumor patient with the cyclophospharnide plus anti-CD3- or anti-CD8-Mab as part of the "microimmunosurgery" can be replaced by the treatment with the cyclophosphamide plus anti-T6 (anti-T9; anti-TlO; anti-TdT)Mab.

The combination of cyclophosphamide with the mixture of Mabs, directed against the mature cells (anti-CD3 Mabs) and T cell precursors (e.g. anti-T6-Mabs) is also recommended.

(22) A combination (a) of antagonists of Gi(Gp)-coupled receptors, (b) of $Ca^{2+}$-influx inhibiting Ca-antagonists, (c) of $Ca^{2+}$-mobilization-inhibiting nitrocompounds, (d) of agonists of Gs-coupled receptors (B-sympathomimetics) and/or (e) of alkalizing agents could be lifesaving even during a fatal immune over-reaction (septic or anaphylactic shock). The K-preparations, $O_2$-scavengers and tolbutarnide or biguanine plus glucose can support this treatment.

(23) The Ts-cells can be converted to the CTL/Tc-cells (and vice versa). The intracellular ADP/ATP-ratio seems to be critical: a n ATP-drop or an ADP-rise seems to signalize the Tc:Ts-interconversion.

A key role seems to play also the ADP/ATP-dependent cAMP/cGMP-ratio. The AMP, formed by the reaction: 2ADP=ATP+AMP, is partly dephosphorylated to adenosine which raises, via A2, the purinergic receptors, the intracellular cAMP-level. The ADP/ATP-decrease (in different stress situations, such as $O_2$-deficit, physical work, cold, heat) is associated by catecholamine (adrenaline)-rise. The adrenaline causes also the rise of intracellular cAMP-level. In order to increase the ADP/ATP-ratio, the following agents are recommended:

(a) $O_2$ or $O_2$-carriers (b) glucose, di- and tricarbonic acids (as alkali-salts), along with antidiabetics (tolbutamide, biguanine etc.), (c) ribose and/or (d) glutamine, glycine and other ATP-precursors. The adenosine or adrenaline-induced cAMP-rise can be inhibited by the corresponding receptor blockers.

(24) The reinduction of tolerance against the tumor cells after removal of primary tumor (a) by surgery and/or (b) by chemotherapy and/or (c) by radiotherapy can be inhibited by the antagonists of Gs-coupled receptors and by ligands of Gi(Gp)-coupled receptors. In the case of B-blockers, the $H_2$-antihistaminics and A2-purinergic blockers, the ligands are directed from Gs- to Gi(Gp)-coupled receptors.

(25) The therapy of (a) lymphomas and (b)leukemias of the T-type can be performed by the "microimmunosurgery" like in solid tumors; again, the sublethal whole body irradiation or high-dose chemotherapy is replaced by the T cell depletion (by Mab-saving cyclophosphamide plus anti-CD3-Mabs). The transformed T cells are eliminated by allogeneic donor effector cells. The mature (post-thymus) malignant cells are MHC II-positive. The immature (pre-thymus) cells are recognized and depleted via blast-specific structures.

(26) Autologous BMT in patients with blood cell tumors and those with solid tumors (e.g. lung cancer) can be improved by the in vitro treatment of autologous BM with allogeneic effector cells whose cell death is preprogrammed. This Ts-depletion on cellular level can be combined with that on humoral level, i.e. with anti-CD8-Mabs and/or with the depletion of contaminating tumor cells ("purgic").

(27) A further elegant technique of deblockade of hyperactivated effector cells and of their reactivation in the short opening of the voltage-operating $Ca^{2+}$-channels (a) by a high frequency (HF)current, or (b) by magnetic induction.

The HF-currents must be significantly lower than those, used in the electroporation or electrofusion (Zimmermann). The deblocked or reactivated state can be "frozen" by Ca-antagonists.

(28) The efficiency of "microimmunosurgery" can be increased by the combination of Gs- and Gi(Gp)-influencing agents.

(29) The disappointing efficacy of (a) LAK- and (b)TIL-cells in vivo can be explained by the cortisol-depression in plasma. Therefore, (a) the use of adrenostatics (e.g.metopiron), inhibiting the 11-B-hydroxylation of glucocorticoids during the LAK- and TIL-infusion, and (b) the admixing of LAK- or TIL-cells, pretransfected in vitro by the cDNA, encoding either the cortisone-cleaving enzyme 20alpha-hydroxysteroid-dehydrogenase (20 alpha SDH) or the cortisone-inactivating enzyme B-glucuronidase, are recommended.

(30) The efficacy of "microimmunosurgery" can be increased also by the pretreatment of the recipient (a) with the BRMs or (b) with the lymphokines (e.g. IFNgamma or IL-4), to render target cells, i.e. pathological subclones more vulnerable.

(31) The standardized "microimmunosurgery" comprises the following steps: (a) Pooled PBs/PBLs or T cells (from donor A,B,C) whose pathogen-specific subclones can be clonally postexpanded in vitro, e.g. by lectins, are (b) "cell death-preprogrammed" and (c) frozen in a medium (e.g. RPMI1640), containing special cryoprotectants (based on PEG and/or PVP) which warrant the preservation of the preactivated cell state, in addition to an improved cell viability. (d) Treatment of patients, suffering e.g. of cancer or autoimmune disorders is restricted to the T cell depletion because the "microimmunosurgery" is based on the simple replacement of the pathologic patient's T set by the healthy donor's T set.

(32) According to a modified "microimmunosurgery"-procedure, the immature T- and B-cell precursors, both of the donor (in vitro) and of the recipient (patient) are eliminated temporarily by specific Mabs or Mabs plus cyclophosphamide; then, the patient's pathological subclones are eradicated and—as the last step—the depleted precursors are replaced by autologous or allogeneic (T-depleted) bone marrow. The special advantage is the early exclusion of inducer and transducer suppressor T cells.

The effector cells can be supported by allogeneic LAK-cells; these can be either premanipulated to express a preprogrammed cell death or depleted of their T cells (10% of cells). In certain situations, the so pretreated allogeneic LAK-cells can be used alone to eliminate the pathologic subclones.

(33) Immunocompetent cells, e.g. macrophages express a variety of additional, not typically "immunologic" receptors (e.g. for the insuline, the glucagon, the parathormone etc.) which have been neglected up to date though they contribute essentially to the activity of immunocompetent cells. The therapeutic manipulation of all these receptors by agonists and antagonists is subject of this invention.

(34) Since the early induction of tolerance involves inducer- and transducer suppressor cells which are both CD4-positive, the use of anti-VD4-Mabs (or immunotoxins) is recommended for the prevention of tolerance in general. An established tolerance, on the other hand, is maintained by mature, CD8-positive Ts cells. The same concerns the reinduction of tolerance against the same antigen. In both cases, the use of anti-CD8-Mabs is recommended. Since immature, CD4-positive inducer and transducer Ts cells are involved in the reinduction of tolerance, anti-CD4-Mab (alone or combined with anti-CD8-Mab) are recommended.

(35) As the IL-2(Tac) receptor (=CD25) is expressed only on (hyper)activated macrophages/monocytes and on the T cells, the parallel depletion of both pathologically hyperactivated subpopulations can be achieved by anti-CD25-Mabs (or immunotoxins). This procedure can improve the "microimmunosurgery" (e.g. in the bone marrow and organ transplantation).

(36) Fibroblasts support the immunosuppressive "tissue repair"/"wound healing"-function of macrophages and increase e.g. their PGE2 secretion. Therefore, the neutralization of specific fibroblast growth factors, e.g. PDGF, bFGF, FAF, FGTB, PF4 and LTBS is recommended.

(37) As pathologic processes, such as GvHR, autoreactivity or sarcoidosis, arise from a mutual stimulation of T4 cells and monocytes/macrophages, the interruption of this activation chain by Mabs against IL-I, TNFalpha and/or IFNgamma is recommended.

(38) Similarly, in BMT the mutual activation cascade, leading to GvH- and HvG-reactivity, has to be interrupted, according to the invention, by neutralizing the involved cytokine(s). The use of Mabs is favorable. It is directed against the TNFalpha, IL-1, IFNgamma, GM-CSF, M-CSF, IL-6 and IL-4.

(39) The combating of residual tumor cells and (premicro) metastases, following tumor excision has best chances if the following 2 principles are combined: (a) $1^{st}$ principle: MHC II-expression on the patient tumor cells, both (a1) by the in vitro MHC II-postexpression, induced by IFNgamma, TNFalpha and/or IL-4, and (a2) by the fusion of tumor cells with autologous or allogeneic MHC II-positive cells (b) $2^{nd}$ principle: transfection of patient tumor cells with cytokines, primarily GM-CSF and IL-4. Before their reinfusion, such modified tumor cells can be manipulated to express the preprogrammed cell death. The local cytokine enrichment can be achieved by the addition of allogeneic B cells.

(40) To increase the humoral response e.g. against HIV, the combination of antibodies of the IgG- or IgM-isotype with those of the IgE-isotype is recommended. The latter can be constructed by the replacement of the Fc gamma or Fcu-subunit by the Fc epsilon-subunit. Alternatively, the IgE-percentage in vivo can be increased by the simultaneous injection of anti-IFNgamma and IL-4(IL-5).

(41) A long-term incubation of PBMs with lectins (e.g. 1 week with ConA or 3 weeks with PHA) leads to a high enrichment of CD8-positive Ts cells; therefore, the depletion of so selected Ts cells (a) by anti-CD8-Mabs (plus complement) or (b) by alloreactive effector cells, with preprogrammed cell death, is recommended. The residual PEMs—released of the depression by the Ts cells—are able to post-generate the Tc/CTLs and Th cells.

In a next procedure, the patient's PBMs are first incubated in vitro with lectins (e.g.PHA) and thereafter treated by increasing concentrations of anti-CD8-Mab (+complement), until the onset of the Tc- and Th-deblockade. Among the deblocked Tc- and Th-cells, tumor-specific clones can be expected; after a further clonal expansion, these tumoricidal subclones can be reinjected into the patient.

(42) During their maturation process, the erythrocytes lose the nuclea. Therefore, the ennucleated precursors (reticulocytes) are of a special interest as carriers of temporarily limited functions (e.g. in vivo production of cytokines, Mabs and suppressor factors or local source of irradiation). In these cells, the cell death need not be preprogrammed.

(43) The controlled DNA-damaging described above ("cell death preprogramming") can be carried out by DNA-selective cytotoxic agents, primarily vinca alkaloids, bleomycin, ICRF-159, busulfan, DDP, VP16231 (EPE) and EPT, in addition to the above mentioned mitomycinC. The controlled DNA-cross-linking can be achieved by so called "bifunctional alkylating agents".

According to a further aspect of the invention, the use of the combination of a Ca-antagonist plus an agent, decreasing the cAMP/cGMP-ratio is recommended as the drug for the treatment of cancer, viral and bacterial infections, as well as autoimmune disorders.

In addition, the use of a combination, consisting of an agent, eliminating hyperactivated effector cells, and of alloreactive cells with preprogrammed cell death is recommended as the drug for the treatment of cancer, viral infections and autoimmune diseases.

According to the invention, an additional approach in the treatment of cancer, viral infections and autoimmune disorders, based on the elimination or down-regulation of immunological effector cells, enables the patient's own immune system to restore the pre-disease state.

What is claimed is:

1. A method of treating solid tumors and herpes viral infections, comprising administering to an affected patient a combination of (I) a Ca-antagonist and (II) an agent to reduce the intracellular cAMP/cGMP-ratio.

2. The method of treating solid tumors and herpes viral infections according to claim 1 wherein the Ca-antagonist is a Ca-overload blocker.

3. The method of treating solid tumors and herpes viral infections according to claim 2 wherein the Ca-antagonist is cinnarizine.

4. The method of treating solid tumors and herpes viral infections according to claim 3 wherein the agent for reducing the intracellular cAMP/cGMP-ratio is selected from the group consisting of a drug decreasing the cAMP-level in the cell, a drug increasing the cGMP-level, and combinations thereof.

5. The method of treating solid tumors and herpes viral infections according to claim 4 wherein the drug decreasing the cAMP-level is selected from the group consisting of antagonists of Gs-coupled receptors, antagonists of Gi/Gp/Go-coupled receptors, and combinations thereof.

6. The method of treating solid tumors and herpes viral infections according to claim 4 wherein the drug decreasing the cAMP-level is selected from the group consisting of antagonists of β-adrenergic receptors, histamine receptors, purinergic receptors, and combinations thereof.

7. The method of treating solid tumors and herpes viral infections according to claim 6 wherein the antagonist of β-adrenergic receptors is propranolol.

8. In the treatment of solid tumors, the step of affecting hyperactivated immunologic effector cells by administering to a patient the combination of (I) an agent eliminating hyperactivated effector cells and (II) alloreactive cells having a predetermined cell death.

9. The method of treating solid tumors according to claim 8 wherein component (I) is a T-cell depleting agent.

10. The method of treating solid tumors according to claim 9 wherein component (I) comprises antibodies against CD8 and/or CD3.

11. The method of treating solid tumors according to any one of claims 1, 9 or 10 wherein component (I) also includes a cytotoxic agent.

12. The method of treating solid tumors according to claim 11 wherein said cytotoxic agent is cyclophosphamide.

13. The method of treating solid tumors according to claim 8 wherein component (II) comprises allogenic cells in which the DNA has been manipulated to inactivate pathological Ts-cells and/or hyperactivated macrophages.

* * * * *